United States Patent [19]

Osuga et al.

[11] Patent Number: 4,716,760
[45] Date of Patent: Jan. 5, 1988

[54] AIR-FUEL RATIO DETECTION SYSTEM

[75] Inventors: Minoru Osuga; Yoshishige Oyama, both of Katsuta, Japan

[73] Assignee: Hitachi, Ltd., Tokyo, Japan

[21] Appl. No.: 833,032

[22] Filed: Feb. 26, 1986

[30] Foreign Application Priority Data

Feb. 28, 1985 [JP] Japan .................................. 60-40198
Apr. 9, 1985 [JP] Japan .................................. 60-74909

[51] Int. Cl.$^4$ .......................................... G01M 15/00
[52] U.S. Cl. ........................................ 73/116; 204/425
[58] Field of Search .............. 73/116; 204/421, 422, 204/423, 424, 425, 426, 427, 428, 429, 408; 123/494

[56] References Cited

U.S. PATENT DOCUMENTS

| | | | |
|---|---|---|---|
| 3,691,023 | 9/1972 | Ruka et al. | 204/1 T |
| 3,907,657 | 9/1975 | Heijne et al. | 204/195 S |
| 4,158,166 | 6/1979 | Isenberg | 324/29 |
| 4,272,331 | 6/1981 | Hetrick | 204/425 X |
| 4,545,889 | 10/1985 | Franx | 204/425 X |
| 4,629,535 | 12/1986 | Oyama et al. | 204/427 X |

FOREIGN PATENT DOCUMENTS 166039 12/1980 Japan .
192852 11/1982 Japan .
103265 7/1984 Japan .
188054 10/1984 Japan .

OTHER PUBLICATIONS

Hetrick, R. E. et al., Oxygen Sensing... Pumping, SAE Technical Paper, No. 810433, Feb. 23, 1981, pp. 63-66.

Primary Examiner—Jerry W. Myracle
Attorney, Agent, or Firm—Antonelli, Terry & Wands

[57] ABSTRACT

A novel air-fuel detection system is disclosed, comprising a solid electrolyte with a diffusion resistor for controlling the oxygen diffusion to measure the air excess rate of an exhaust gas. A predetermined current is supplied to the solid electrolyte for a predetermined length of time to apply the oxygen into the diffusion resistor. Subsequently, a predetermined current of opposite polarity is supplied to the solid electrolyte for a predetermined length of time to draw the oxygen out of the diffusion resistor. The time required from the start of drawing to generation of an electromotive force due to the difference in oxygen component pressures between the sides of the solid electrolyte is measured and the above operations are alternatively repeated in the time sharing manner to determine the air-fuel ratio.

36 Claims, 48 Drawing Figures

FIG. 3A
(a)
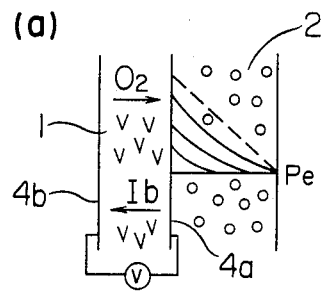
(b)
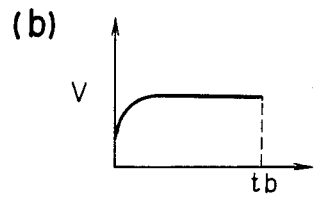
FIG. 3B
(a) LEAN
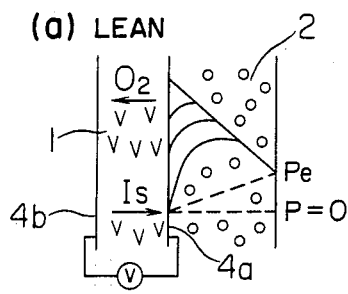
(b)
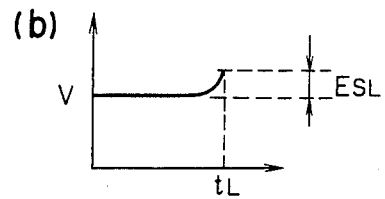
FIG. 3C
(a) RICH
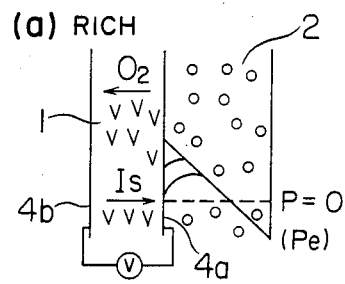
(b)
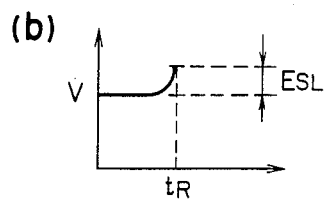

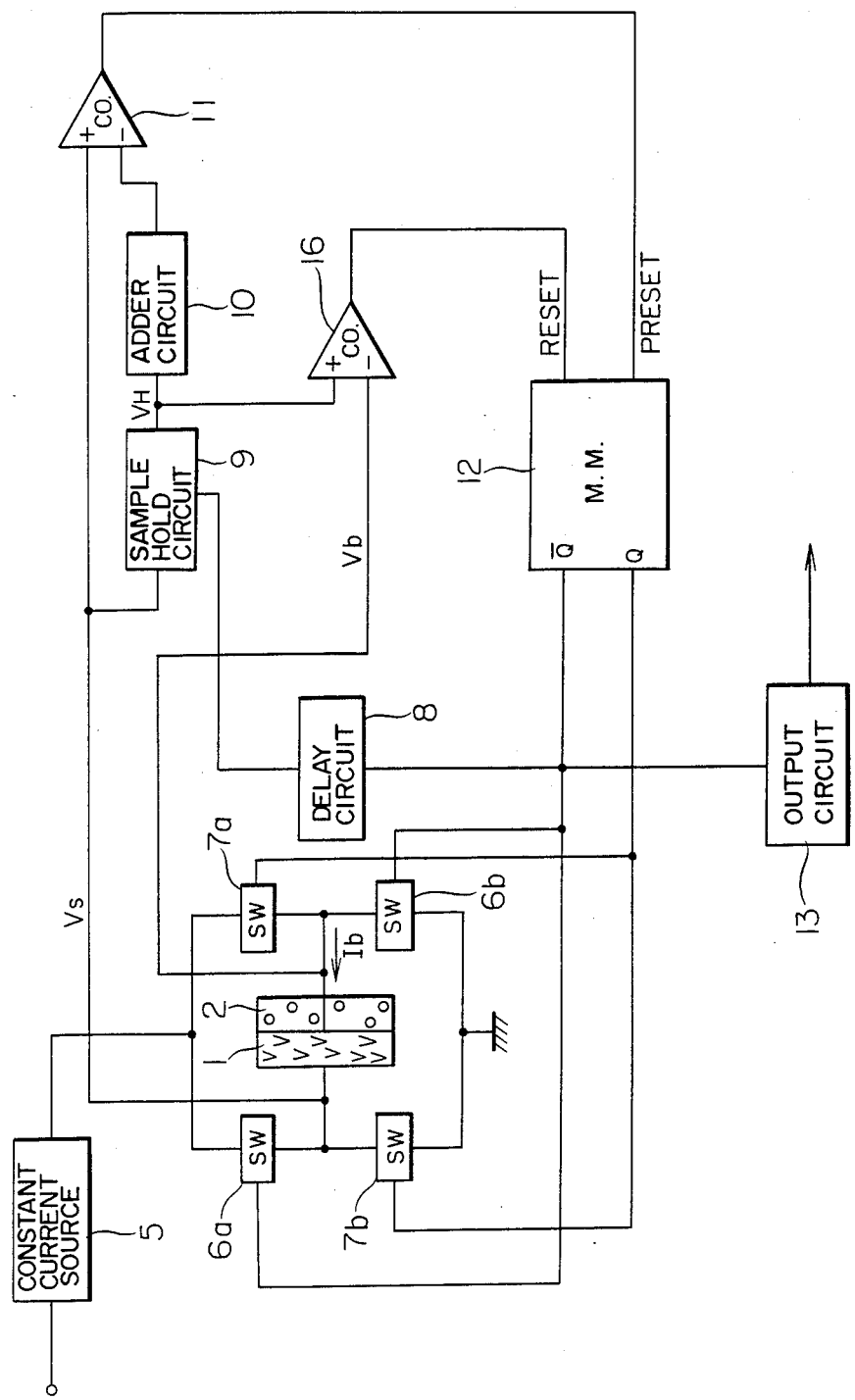

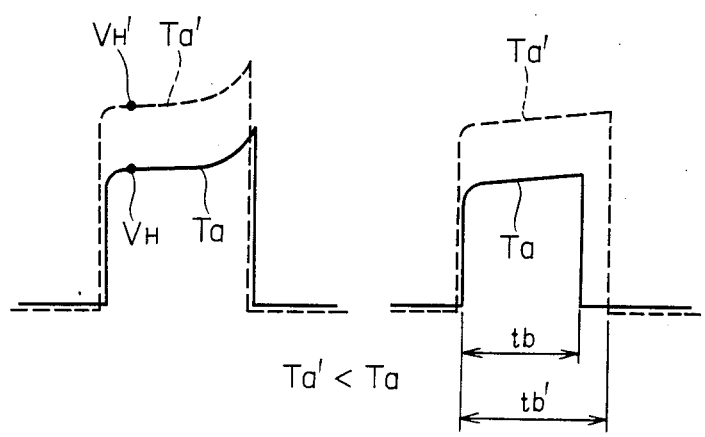

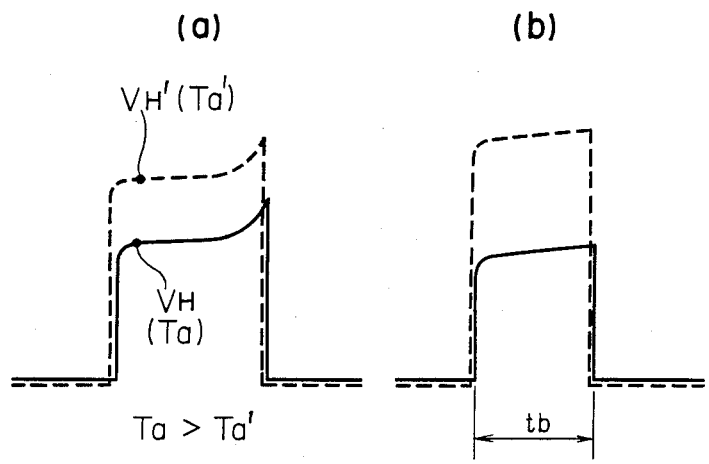
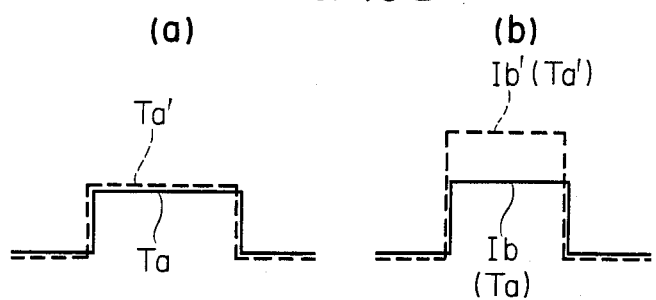

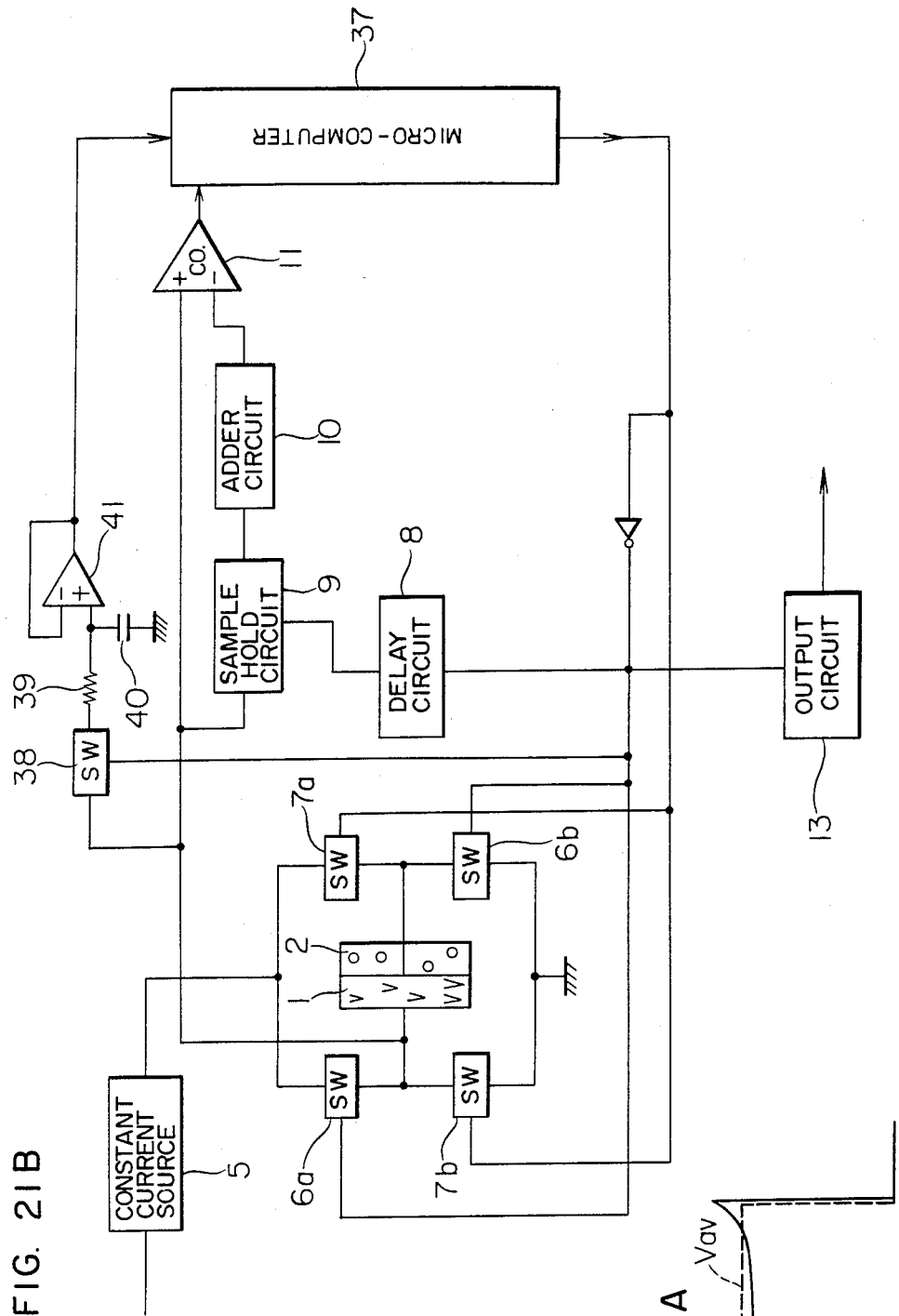

AIR-FUEL RATIO DETECTION SYSTEM

BACKGROUND OF THE INVENTION

The present invention relates to a system for detecting the air-fuel ratio, or more in particular to an air-fuel ratio detection system capable of using a system for controlling the air-fuel ratio of an internal combustion engine.

A conventional air-fuel ratio sensor, as disclosed in U.S. Pat. Nos. 3,691,023 and 4,158,166, comprises a solid electrolyte having a diffusion resistor and operates in such a manner that the oxygen is drawn out of the diffusion resistor and a measurement is taken of a current value as of the time when the concentration of the oxygen is reduced to zero (what is called the critical current value). In this method, the measurement of the air excess rate $\lambda$ is possible only in the region where the oxygen is contained in the gas to be measured, that is, in the region where the air excess rate is 1.0 or more, while if the value $\lambda$ is less than 1.0 it is impossible to measure the value $\lambda$.

Also when measuring the region where the value $\lambda$ is smaller than 1.0, it is necessary to reverse the voltage applied to the solid electrolyte at the point 1.0 in the value $\lambda$ as indicated in Japanese Patent Unexamined Publication No. 166039/80. This requires a new means for detecting the point where $\lambda$ is 1.0, complicating the system.

According to the method disclosed in SAE paper 810433 shown in FIG. 12, on the other hand, the current is applied to one solid electrolyte while being reversed in polarity, and by loading and unloading the oxygen in a chamber, the oxygen concentration in the chamber is changed, so that the change in electromotive force with the concentration is detected by the other solid electrolyte. The polarity is reversed each time the electromotive force reaches a predetermined value, and the fact is taken advantage of that the period of this reversal is proportional to the oxygen concentration. In another method disclosed in U.S. Pat. No. 3,907,657, the oxygen diffused in a chamber is drawn out by a current, and the time $\tau$ before the oxygen concentration in the chamber is reduced to zero is counted from the change in electromotive force between the electrodes on the solid electrolyte, utilizing the phenomenon that the value $\tau$ is proportional to the oxygen concentration The absolute amount of oxygen in a chamber of a predetermined volume is measured in both the methods, which are liable to be affected by the secular variations in the volume and temperature or pressure. Further, the predetermined volume is formed by a single aperture, and the effect is great if the aperture is clogged. Still another disadvantages of these systems is that since the whole sensor is exposed to the combusion exhaust gas, it is impossible to measure the value $\lambda$ in the region where it is smaller than 1.0.

A further conventional system is disclosed in Japanese Patent Unexamined Publication No. 192852/82, in which a means for detecting the temperature of a solid electrolyte comprises an alternating current with the solid electrolyte, a period of temperature measurement, or a temperature-measuring device. A method is also known in which the temperature of the electrolyte is estimated from the operating conditions of an engine or the temperature of the exhaust gas thereof (Japanese Utility Model Unexamined Publication No. 103265/84, Japanese Patent Unexamined Publication No. 188054/84). These systems, however, have a complicated construction or an insufficient accuracy of temperature detection which is effected indirectly.

SUMMARY OF THE INVENTION

The object of the present invention is to provide an air-fuel ratio detection system which is capable of detecting the air excess rate in a wide range without being affected by temperature changes.

According to the present invention, there is provided a system and a method in which after oxygen is supplied into a diffusion resistor by a solid electrolyte, the oxygen is drawn out of the diffusion resistor in reverse way, and the oxygen concentration is measured from the change in the amount of electricity with the movement of the oxygen, so that the air excess rate is detected over a wide range without being affected by temperature changes.

BRIEF DESCRIPTION OF THE DRAWINGS

FIGS. 3A, 3B and 3C are diagrams for explaining the fundamental operating principle of the present invention.

FIG. 10 is a diagram showing a general configuration for realizing the embodiment explained with reference to FIGS. 9A, 9B and 9C.

FIGS. 11A, 11B and 12 are diagrams showing still another embodiment.

FIGS. 13A, 13B and 14 are diagrams showing a further embodiment.

FIGS. 21A and 21B are diagrams showing a still different embodiment.

DESCRIPTION OF THE PREFERRED EMBODIMENTS

Figure 1:
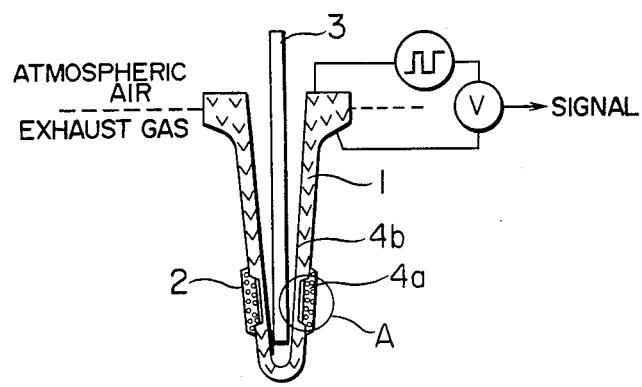
FIG. 1 is a diagram for explaining an embodiment of the sensor according to the present invention.
Figure 2:
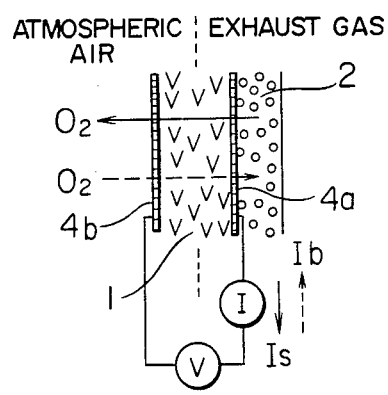
FIG. 2 is a diagram showing in an enlarged manner the essential parts surrounded by a circle in FIG. 1A.

Prior to explaining a configuration and operation of the present invention, explanation will be made of the principle providing a base thereof with reference to FIGS. 1 to 6C. A porous diffused resistor 2 is arranged on the exhaust side of a solid electrolyte 1. The solid electrolyte 1 is in the shape of a tubular case, into which atmospheric air is introduced. Further, a heater 3 is contained in the solid electrolyte 1. The solid electrolyte 1 has electrodes 4a and 4b on the exhaust and atmospheric sides thereof. These electrodes are impressed with a predetermined current alternately in forward and reverse directions in a time sharing manner by a constant current circuit, and an output is produced by the change in the terminal voltage V involved. FIG. 2 is an enlarged view of the part surrounded by a circle in FIG. 1. This sensor is provided for the purpose of measuring the air-fuel ratio, and reverses the direction of the current applied to the solid electrolyte 1 in a time sharing manner. In operation, as shown in FIG. 2, first, the current Ib is applied in the direction shown by arrow of dashed line in FIG. 2 to introduce the oxygen from the atmosphere into the porous diffusion resistor 2 in the exhaust air as shown by arrow of dashed line in FIG. 2. Then, the current Ia is applied in the reverse direction (arrow of solid line) thereby to draw the oxygen out of the diffused resistor 2 in the direction shown by arrow of solid line. The former operation is called the bias operation, and the latter the sensing operation.

FIGS. 3A to 3C show a change in the distribution of the oxygen concentration in the diffusion resistor 2 (solid curve in the drawing), and a change in the terminal voltage V of the solid electrolyte 1. FIG. 3A(a) is a diagram associated with the bias operation, in which the graph depicted in the diffusion resistor 2 represents the position in the diffusion resistor along the abscissa, and the oxygen concentration at the corresponding position along the ordinate thereof. When oxygen is introduced into the diffusion resistor 2 by application of the current Ib, the distribution of the oxygen concentration in the diffusion resistor 2 changes in such a manner that the oxygen concentration on the solid electrolyte 1 side becomes higher than that of the exhaust gas on the exhaust side, and therefore the curve changes in position from the lower to upper one. Soon after that, when the amount of the oxygen introduced into the electrode 4a through the solid electrolyte 1 is balanced with the amount of the oxygen diffused into the exhaust gas through the diffusion resistor 2, the distribution curve is converged to a shape as shown by the dashed line in FIG. 3A(a). As a result, the terminal voltage V also increases with the oxygen concentration of the electrode 4a as shown in FIG. 3A(b), and soon converges to a fixed value. Under this condition, V is given as $$V = rIb - \frac{RT}{4F} \ln \frac{P(4b)}{P(4a)} \tag{1}$$

where
r: Internal resistance of the solid electrolyte 1
T: Temperature of the solid electrolyte 1
R: Gas constant
F: Faraday constant
P(4a): Oxygen concentration on electrode 4a side
P(4b): Oxygen concentration on electrode 4b side The second term on the right side represents the electromotive force which sharply increases when the value P(4a) approaches zero during the sensing operation.

The change in the distribution of oxygen concentration in the diffusion resistor 5, on the other hand, is determined from the following diffusion equation:

$$\frac{\partial P}{\partial t} = D \frac{\partial^2 P}{\partial x^2} \tag{2}$$

$$B \cdot C_1 \frac{\partial P}{\partial x} + \frac{Ib}{C} = 0 \tag{3}$$

where D is the diffusion coefficient, t the time, x the distance, P the oxygen concentration, and C a constant.

FIGS. 3B and 3C show the conditions under the sensing operation. FIG. 3B is associated with the lean air-fuel mixture, and the FIG. 3C the rich one. Under this condition, the terminal voltage is expressed as $$V = rIs + \frac{RT}{4F} \ln \frac{P(4b)}{P(4a)} \tag{4}$$

In FIG. 3B(a), when oxygen is drawn out of the diffusion resistor 2 by application of the current Is, the oxygen concentration distribution moves from the upper curve to the lower curve, and the oxygen concentration P(4a) on the electrode 4a side gradually decreases and soon approaches zero. At this time, the electromotive force in the second term on the right side of equation (4) increases sharply, while the voltage V also sharply increases as shown in FIG. 3B(b). If the sensing operation ends when the increment due to the electromotive force reaches a predetermined value $E_{SL}$, the period of the sensing operation $t_L$ takes a value proportional to the air-fuel ratio. As will be seen, in the initial stage of the sensing operation, oxygen exists near the electrode 4a, and therefore the value of the second term of the right side of equation (4) is very small, so that the first term thereof is controlling. While the oxygen on and near the electrode 4a is depleted, on the other hand, the value of the second term of the right side suddenly increases, with the result that the value V increases sharply, and by detecting this, it is possible to measure the sensing time. FIG. 3C(a) shows a case associated with the rich air-fuel ratio, in which the oxygen concentration distribution after the bias operation is such that the oxygen is consumed by the reaction with the combustible gases (CO, HC, $H_2$) diffused from the exhaust side, causing a region of P=0 in the diffusion resistor. As a result, the amount of oxygen drawn out at the time of sensing operation is reduced, and as shown in FIG. 3C(b), the $t_R$ required before the change of V reaches $E_{SL}$ is smaller than the time $t_L$. In this way, the oxygen concentration P(4a) near the electrode 4a may be made larger than the oxygen concentration Pe of the exhaust gas by supplying oxygen into the diffusion resistor by the bias operation, and therefore it is possible to measure the air-fuel ratio even when the value λ is smaller than unity.

Figure 4A:
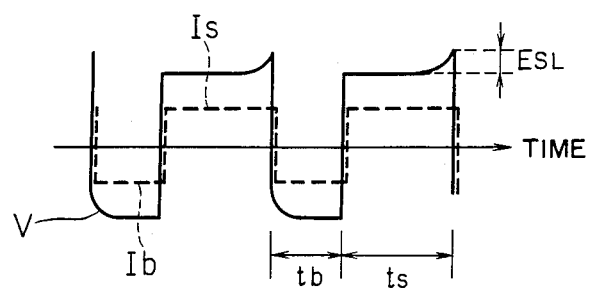
FIG. 4A is a waveform diagram showing the relationship between the current supplied to a solid electrolyte and the voltage appearing across the sides of the solid electrolyte.
Figure 4B:
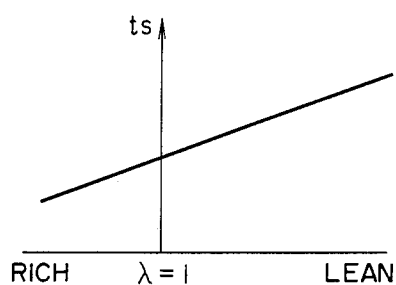
FIG. 4B is a diagram showing an output characteristic indicating the relationship between the air excess rate and the sensing operation.

FIG. 4A shows a timing chart for Is, Ib and V. As shown in FIG. 4A, the currents Ib and Is are supplied while being reversed in direction in a time sharing manner. With the currents Ib and Is and the bias operation time $t_b$ fixed, the current direction is reversed at the time point when the predetermined value $E_{SL}$ is reached by the increment of the voltage V. The air-fuel ratio is determined by counting the time $t_s$ involved. An output characteristic of this system is shown in FIG. 4B, in which $t_s$ is proportional to the air-fuel ratio over a wide range from rich to lean charge.

Figure 5:
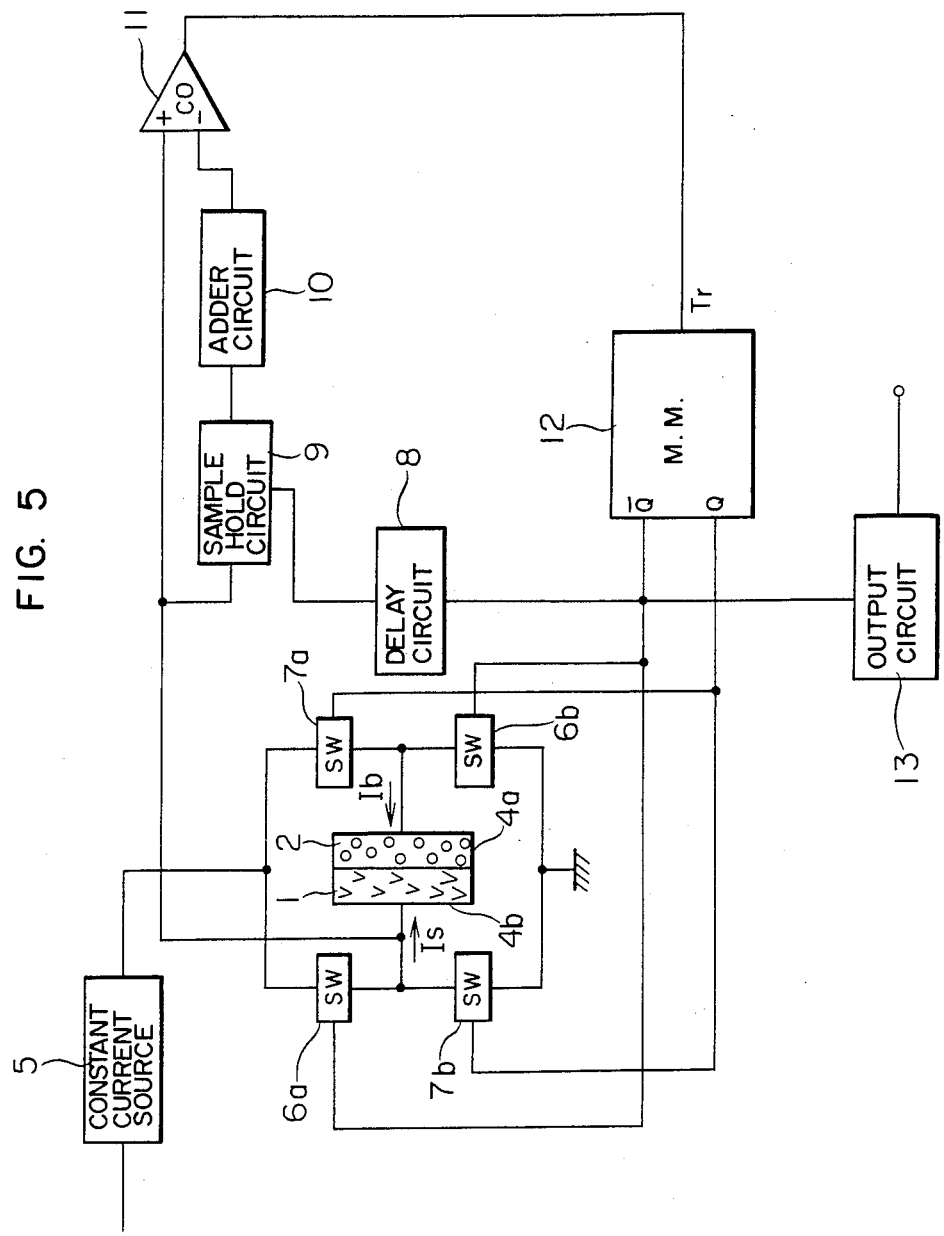
FIG. 5 is a diagram showing a circuit for driving a sensor.
Figure 6A:
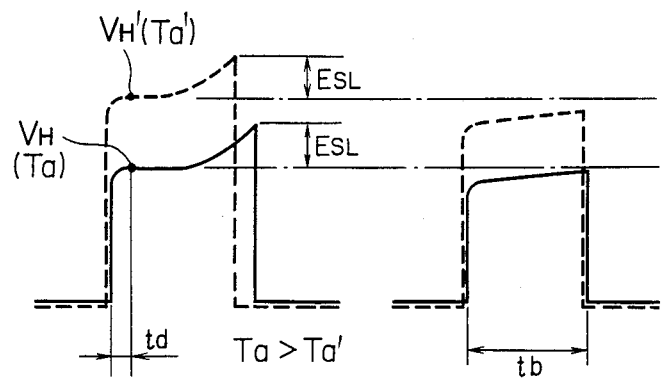
FIGS. 6A, 6B and 6C are diagrams for explaining the operating principle of the present invention.

FIG. 5 shows an embodiment of a circuit for effecting the operation of the sensor. Numeral 5 designates a constant current source. When switches 6a and 6b are turned on with switches 7a and 7b off, the current Ia flows in the solid electrolyte 1 for effecting the sensing operation. If the switches 6a and 6b are turned off with the switches 7a and 7b on, on the other hand, the current Ib flows for bias operation. In the case shown, Is=Ib. The operation of this circuit will be explained below with reference to the waveforms shown in FIG. 6A. First, an on signal is applied to the switches 6a and 6b to start the sensing operation (FIG. 6A(a)). The on signal is applied to a delay circuit 8, and as shown in FIG. 6A, after the transient period $t_d$, the on signal is produced to a sample hold circuit 9. The sample hold circuit 9 holds the terminal voltage $V_H$ the time $t_4$ after the start of the sensing operation. This voltage $V_H$ is combined with the voltage $E_{SL}$ by the adder circuit 10 and applied to a comparator 11. The comparator 11 produces a trigger signal Tr when the terminal voltage V exceeds the value $V_H+E_{SL}$. This trigger signal is applied to a monostable multivibrator 12, in which the terminal $\overline{Q}$ is kept off and Q on during the period $t_b$ after application of the trigger signal. Specifically, during the time $t_b$, the switches 7a and 7b are supplied with an on signal, and the switches 6a and 6b with an off signal for bias operation. (FIG. 6A(b)) With the lapse of time $t_b$, the terminal $\overline{Q}$ of the multivibrator 12 is turned on and the terminal Q thereof turned off again, thus starting the sensing operation. The output is produced by an output circuit 13 for converting the time $t_s$ during which the terminal $\overline{Q}$ is kept on into an analog output. This analog output is converted into a value corresponding to the air-fuel ratio.

The voltage $V_H$ held takes a value almost equal to rI shown in equations (1) and (4), which is dependent on the internal resistance r of the solid electrolyte 1 (∴ Ib=Is=Constant), and since the value r is dependent on the temperature, represents the temperature of the solid electrolyte 1 at the same time.

Figure 6B:
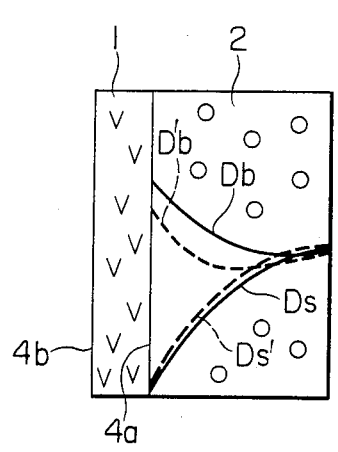
Figure 6C:
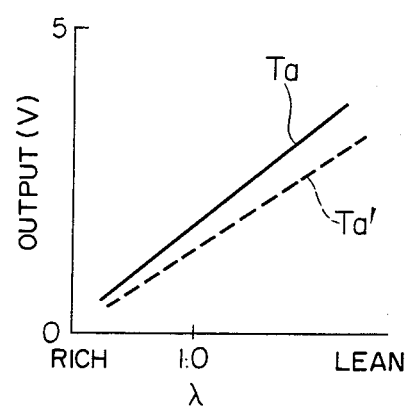

Explanation will be made now of the manner in which the waveform changes with the change of the ambient temperature from Ta to Ta'. (Ta>Ta'), with reference to FIGS. 6A to 6C. FIG. 6A(a) shows a waveform obtained during the sensing operation, and FIG. 6A(b) a waveform for bias operation. When the temperature falls from Ta to Ta', the voltage $V_H$ increases to $V_H'$. (Equations (1) and (4)) If the same value $E_{SL}$ is taken for both the cases, the sensing time $t_s'$ is shorter for Ta'. The bias waveform of FIG. 6A(b) remains unchanged as $t_b$ is constant, so that the absolute value is larger for Ta', thus causing an error of $t_s$ according to the temperature. The reason why an error occurs of the value $t_s$ will be explained by reference to FIG. 6B, showing the oxygen concentration distribution in the diffusion resistor 2. The distribution Ds (distribution in sensing action) is the one at the end of the sensing operation, and the distribution Db (distribution in bias action) is the one at the end of the bias operation. The characters Ds' and Db' respectively show the distributions at the temperature Ta'. If Ib, Is, $t_b$ and $E_{SL}$ take a fixed value respectively, there occurs a difference between Ds and Ds' and between Db and Db'. This is because the diffusion speed of oxygen in the diffusion resistor 2 varies with the temperature difference. Since the value $E_{SL}$ is fixed, Ds and Ds' have almost the same distribution because oxygen is drawn out until the value P(4a) at the electrode 4a becomes almost zero. Since the value $t_b$ is constant, on the other hand, Db and Db' develop a difference by the difference in oxygen diffusion speed, so that the curve Db represents a generally higher concentration distribution than Db'. As explained above, with a change in ambient temperature, the difference in the manner of change of the oxygen concentration distribution attributable to the oxygen diffusion speed causes a change in the value $t_s$. Since $t_s'$ becomes smaller than $t_s$, the output of the output circuit 13 is smaller for Ta' than for Ta, thereby causing an error with temperature.

Explanation will be made below of various methods and systems for eliminating the adverse effects of this temperature change on the measurement.

Figure 7:
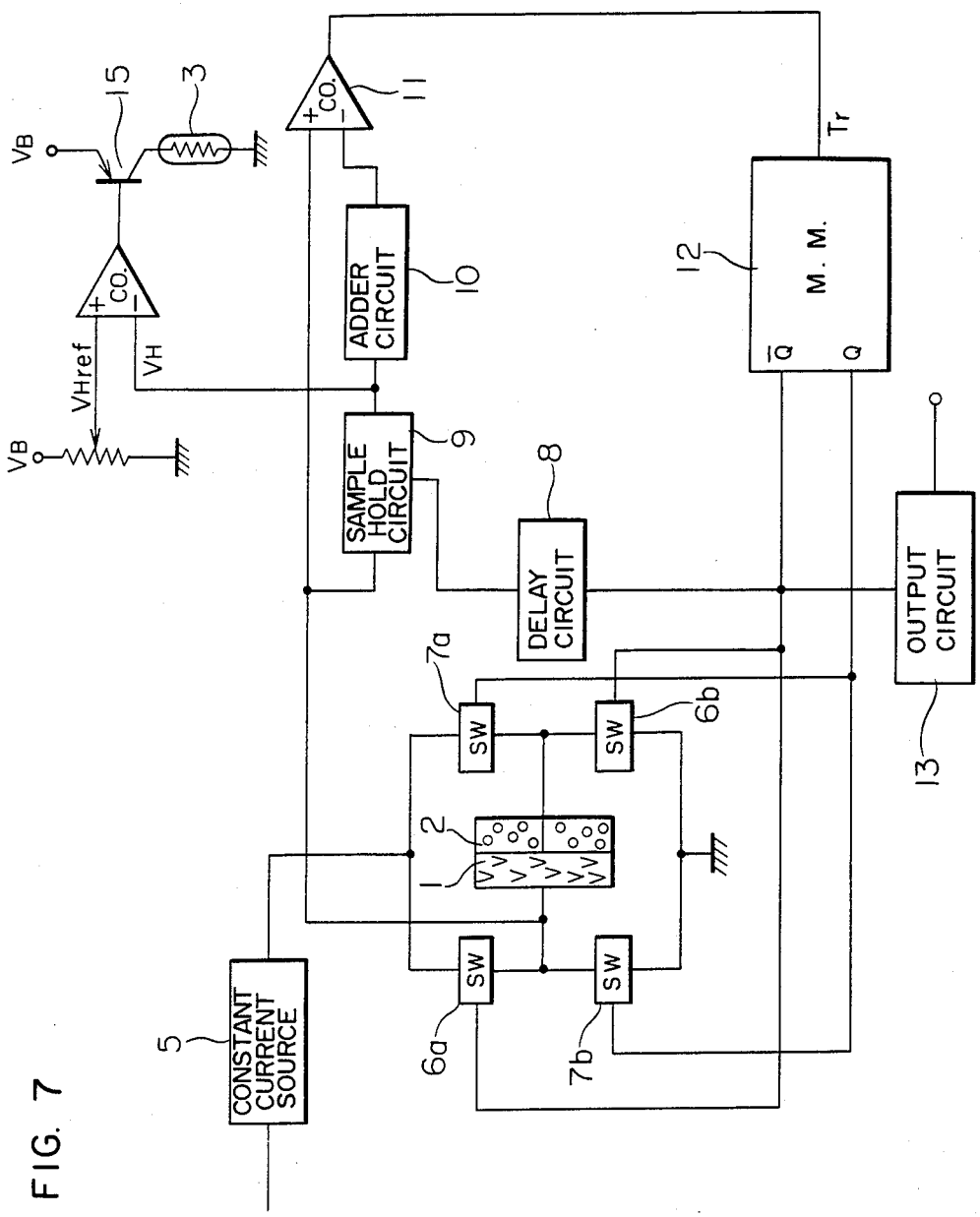
FIG. 7 is a diagram showing a general configuration of an embodiment of the present invention.

FIG. 7 is a diagram showing an embodiment of a circuit for preventing an error with temperature change. The voltage $V_H$ held by the sample hold circuit 9 (a value representing the internal resistance) is compared with a predetermined value $V_{Href}$ at a comparator 14, and when $V_H$ is smaller than $V_{Href}$, an on signal is applied to the base of a transistor 15 thereby to de-energize the transistor 15, thereby stopping the energization of a heater 3. The relations $V_H < V_{Href}$ represents the case in which the internal resistance r of the solid electrolyte 1 is small, that is, the temperature is higher than the setting, in which case the energization of the heater 3 is stopped as mentioned above. When the voltage $V_H$ exceeds the voltage $V_{Href}$, on the other hand, the comparator 14 applies an off signal to the base of the transistor 15, thus energizing the heater 3. That is to say, when the temperature of the solid electrolyte 1 becomes lower than a set temperature, the heater 3 is actuated. In this way, the voltage $V_H$ can be controlled at the value $V_{Href}$ so that the temperature of the solid electrolyte 1 is maintained at a predetermined level. As a result, it is possible to detect the air-fuel ratio without regard to the ambient temperature.

Figure 8A:
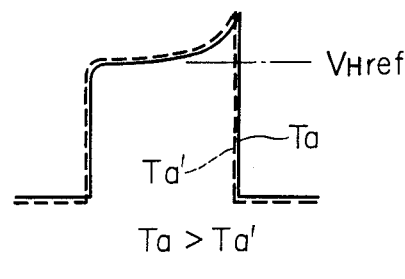
FIGS. 8A to 8D are diagrams for explaining the operating principle and the effects of the embodiment shown in FIG. 7.
Figure 8B:
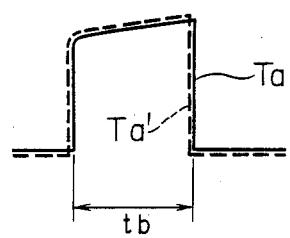
Figure 8C:
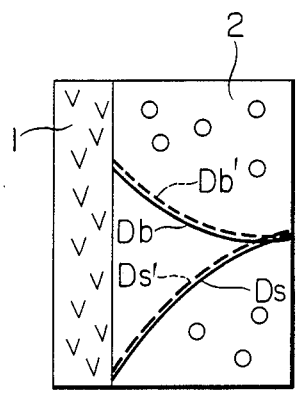
Figure 8D:
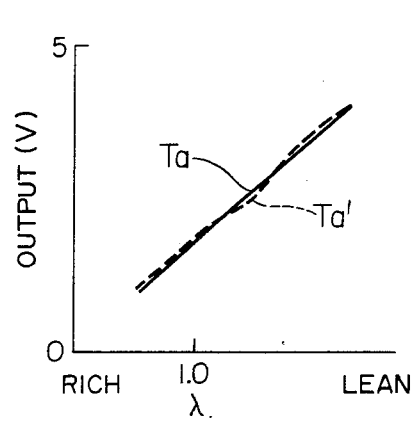

FIGS. 8A to 8D show the operating principle of the circuit shown in FIG. 7 and the result of an experiment thereon. In view of the fact that the temperature of the solid electrolyte 1 is kept at a fixed value, the waveform during the sensing operation in FIG. 8A takes the same form as that during the bias operation of FIG. 8B for both the curves Ta and Ta'. As shown in FIG. 8C, on the other hand, the distribution of Ds, Ds' and Db and Db' is also the same. An output value measured on the abovementioned principle is shown in FIG. 8D. Since the temperature of the solid electrolyte 1 is kept fixed by the control of the heater 3 despite the difference between Ta and Ta' in ambient temperature, the outputs are coincident with each other for the curves Ta and Ta'.

Figure 9A:
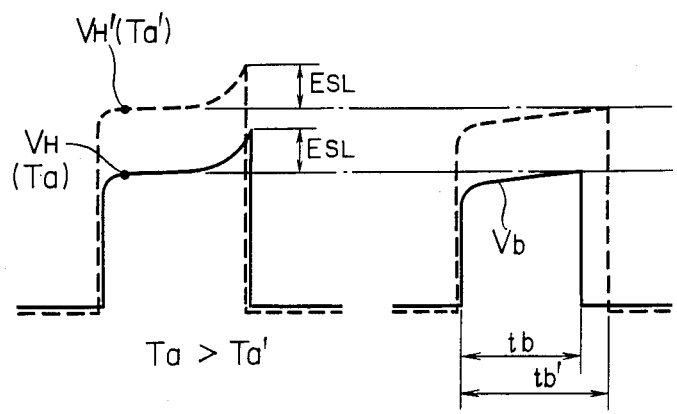
FIGS. 9A, 9B and 9C are diagrams for explaining the operation of another embodiment of the present invention.
Figure 9B:
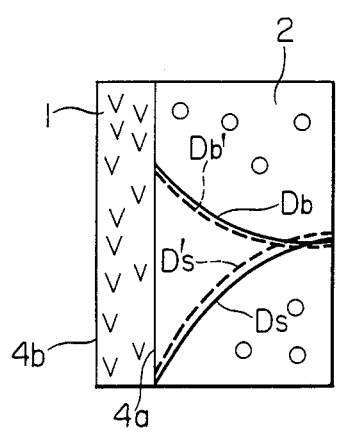
Figure 9C:
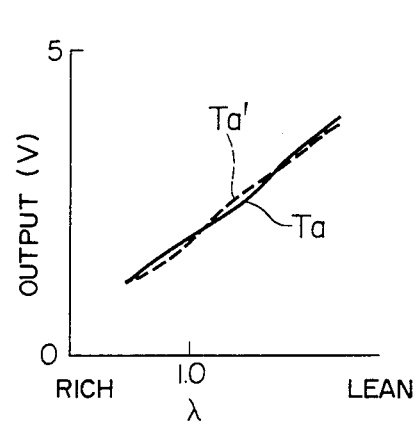

Another principle of temperature compensation is shown in FIGS. 9A to 9C. In these diagrams, Is=Ib=-Constant, and $E_{SL}$ is constant. As shown in FIG. 9A(a), the volta $V_H$ or $V_{H'}$ held at the time of the sensing operation is kept held until the time of bias operation (FIG. 9A(b)), when the terminal voltage Vb becomes equal to the $V_H$ during the bias operation, the bias operation is terminated. As a result, when the temperature Ta' and the ambient temperature are low, the time $t_{b'}$ and the bias time are lengthened, thus eliminating the difference between the sensing times $t_s$ and $t_{s'}$. This principle is shown in FIG. 9A(b). That the terminal voltage Vb at the end of the bias operation is made equal to $V_H$ (the terminal voltage at the start of the sensing operation) corresponds to the fact that the equation (1) becomes equal to the value V of equation (4), and this condition is given by the relations $$P(4a) = P(4b) \quad (5)$$

Specifically, since P(4b) represents the oxygen concentration of the atmospheric air, P(4a) increases almost to the level of the oxygen concentration of the atmospheric air. That is to say, the value P(4a) increases until it becomes fixed for each cycle without regard to the ambient temperature (Ta, Ta'), and therefore both Db and Db' have almost the same distribution. As a consequence, the difference between Db and Db' as indicated in FIG. 6B is eliminated, and the curves as shown in FIG. 9B are realized, thus producing the value $t_s$ not affected by the temperature. FIG. 9C shows the result of an actual measurement, indicating that with the change in ambient temperature from Ta to Ta', the bias time $t_b$ is lengthened to $t_{b'}$, and therefore an output is produced without being affected by the ambient temperature.

FIG. 10 shows an embodiment of the circuit for embodying the operating principle of FIGS. 9A to 9C. The voltage $V_H$ held at the sample hold circuit 9 is applied to the comparator 16 for comparing it with the terminal voltage Vb associated with the current Ib flowing during the bias operation. When the voltages Vb and $V_H$ become equal to each other, the comparator 16 produces an off signal, which is in turn applied to the reset terminal of the monostable multivibrator 12, so that the terminal $\overline{Q}$ is turned on and the terminal Q turned off, while the switches 6a and 6b are turned on, with the switches 7a and 7b turned off. Then, the voltage Vb is reduced to the earth potential, the comparator 16 is turned on, and the multivibrator 12 is kept on at $\overline{Q}$ and off at Q. When the change of the terminal voltage Vb is increased beyond the voltage $E_{SL}$ during the sensing operation, on the other hand, the comparator 11 is turned off. This off signal is applied to the preset terminal of the multivibrator 12, with the result that the terminal $\overline{Q}$ is turned off and Q turned on for starting the bias operation. At the time, the voltage Bs is grounded, as a result, the comparator 11 is immediately turned on and therefore the multivibrator 12 is kept off at $\overline{Q}$ and on at Q. As mentioned above, the circuit of FIG. 10 carries out the compensating operation shown in FIG. 9, thereby producing a temperature-compensated output automatically.

Figure 12:
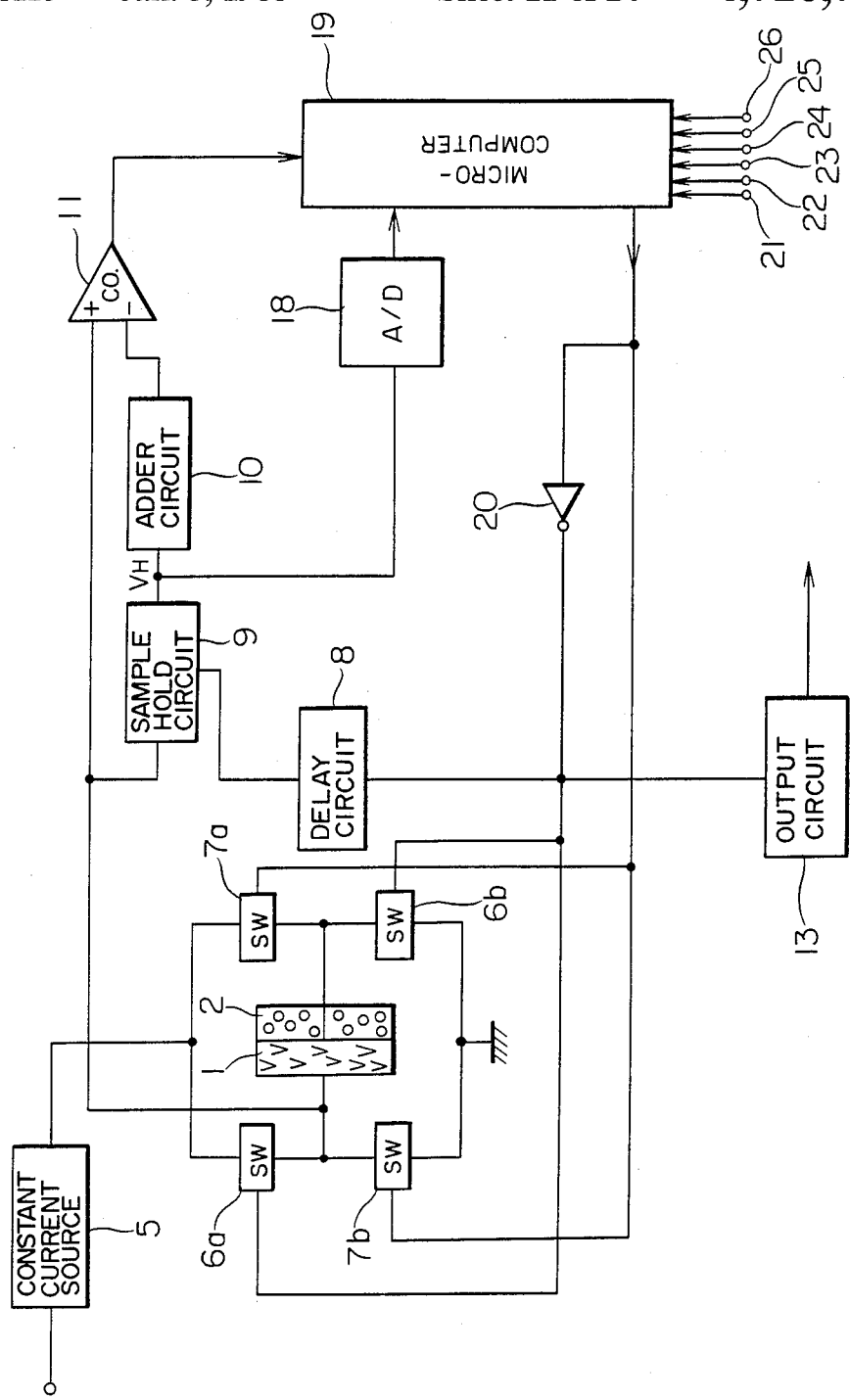

As will be seen from the above description, in the case where the temperature of the solid electrolyte 1 is low, the bias time should be lengthened. In the system shown in FIGS. 9A to 10, the value $t_b$ undergoes a change automatically, while the system of FIGS. 11A to 12 is the one for forcibly changing the value $t_b$. Specifically, it is a configuration in which, as shown in FIG. 11, when the temperature changes from Ta to Ta', the change in $V_H$ and $V_{H'}$, is detected, and with this change, the time $t_b$ is lengthened to $t_{b'}$, with the result that the bias time is lengthened to maintain the output constant. An embodiment of the circuit for realizing this configuration is shown in FIG. 12. In FIG. 12, the voltage $V_H$ held by the sample hold circuit 9 is introduced into the microcomputer 19 through the A/D converter 18. By a positive (+) trigger signal of the comparator 11 indicating the end of the sensing operation, a signal is produced which is turned on only during the bias time $t_b$ read on the basis of the voltage $V_H$ from a table showing the relationship between $V_H$ and $t_b$ experimentally determined in advance in the microcomputer 19. This on signal turns on the switches 7a and 7b, and by the action of the inverter 20, the switches 6a and 6b are turned off, so that the bias operation is continued for the time $t_b$. Upon the lapse of the bias time $t_b$, the output from the computer 19 is turned off, and the switches 7a and 7b are turned off. At the same time, the operation of the inverter 20 turns on the switches 6a and 6b, thereby starting the sensing operation. When the output voltage $V_H$ increases to $V_{H'}$, the bias time $t_b$ is lengthened to $t_{b'}$. In the microcomputer 19, the bias time $t_b$ may be corrected in accordance with the r.p.m signal 21, the load signal 22, the intake air amount 23, the cooling water temperature 24, the intake air temperature 25 or the exhaust air temperature 26.

Figure 14:
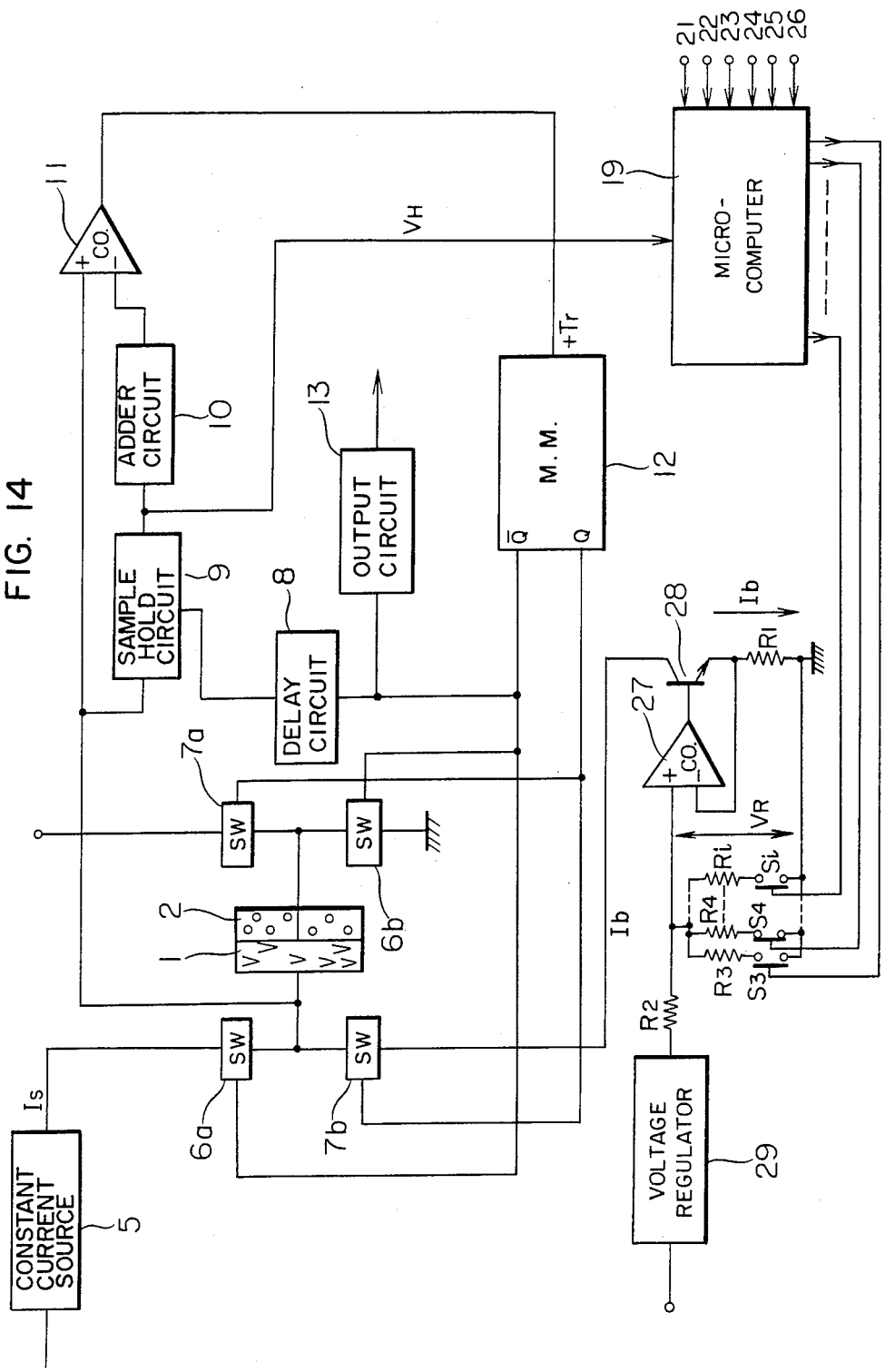

FIGS. 13A to 14 show another configuration of the temperature compensation circuit. In this configuration, when the ambient temperature Ta changes to Ta', the bias time $t_b$ remains unchanged, while the current value Ib flowing during the bias operation is changed. Specifically, the amount of change of Ta is detected from the amount of change of $V_H$, so as to change the bias current Ib. In the case where the ambient temperature Ta is low at Ta', the bias current Ib is increased to Ib' (FIG. 13B(b)), thereby keeping the same bias oxygen amount for the same bias time. The result is that the same effect is obtained as if the bias time has actually been lengthened, thereby eliminating the temperature dependency of the output. As shown in FIG. 13B(a), the current is kept the same at the time of sensing operation.

FIG. 14 shows a circuit configuration which is basically the same as the one shown in FIG. 5, but is different in that in the circuit configuration of FIG. 14, a different constant current source is used for the current Ib for bias operation from the constant current source for the current Is for the sensing operation. In FIG. 14, the bias current Ib is produced in the manner mentioned below. Specifically, the voltage across a resistor $R_1$ is controlled to take a value $V_R$ by the action of an operational amplifier 27 and a transistor 28. As a result, the bias current Ib is determined from the relationship $$Ib = \frac{V_R}{R_1} \quad (6)$$

where $V_R$ is determined by a voltage regulator 29, resistors $R_2$, $R_3$, $R_4$, ... $R_i$, switches $S_3$, $S_4$, ... $S_i$. In other words, on the basis of the $V_H$ applied into the microcomputer 19, the value Ib is determined from a table experimentally formed in advance, so that the value Ib is produced by turning on a predetermined number of switches $S_3$, $S_4$, ... $S_i$. In this way, a large current Ib can be supplied to the sensor when the voltage $V_H$ is increased, and vice versa.

Figure 15A:
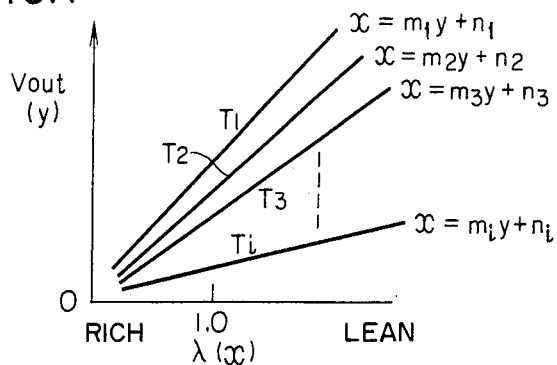
FIGS. 15A and 15B are diagrams showing a still further embodiment.
Figure 15B:
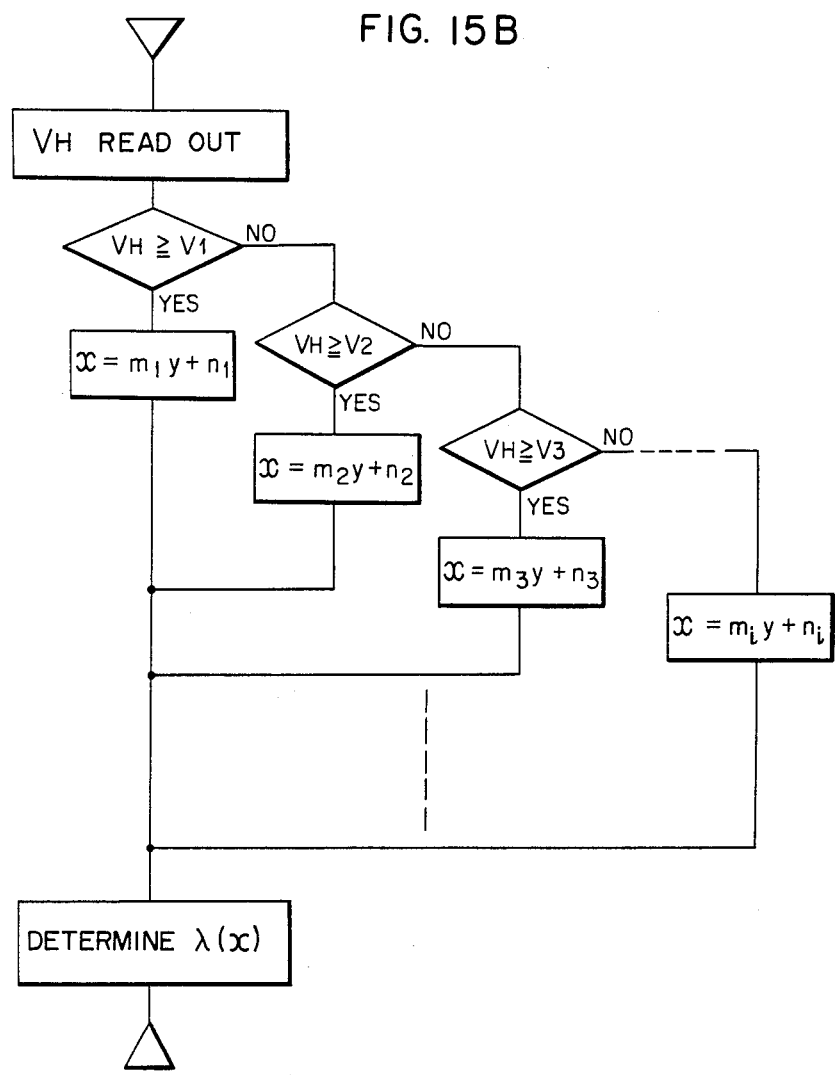

FIGS. 15A and 15B show another embodiment. The circuit configuration of this embodiment may be the same as that of FIGS. 5 and 7. As to the output of the sensor in this embodiment, with the decrease in the temperature of the solid electrolyte 1 from $T_1$ to $T_2$ to $T_3 \ldots T_i$, the relationship between the air-fuel ratio $\lambda$ and the output Vout changes as shown in FIG. 15A. If this relationship is approximated by a linear equation, for example, with the air-fuel ratio $\lambda$ taken along the abscissa and the output Vout along the ordinate, then $x = m_1 y + n_1$ for the temperature $T_1$, $x = m_2 y + n_2$ for the temperature $T_2$, $x = m_3 y + n_3$ for the temperature $T_3$,

.
.
.

$x = m_i y + n_i$ for the temperature $T_i$.

These factors $m_1, \ldots m_i$, and $n_1, \ldots n_i$ are stored in the microcomputer in the form of a table determined experimentally in advance, so that when the air-fuel ratio $\lambda$ is determined as shown in FIG. 15B by introducing the sample-held value $V_H$ into the computer, the factors $m_1$, $n_1$ are used if the $V_H$ is larger than a given value $V_1$, while if $V_1 > V_H \geq V_2$, the factors $m_2$, $n_2$ are used. By using different factors for determining the air-fuel ratio $\lambda$ according to the value $V_H$ in this way, the correct air-fuel ratio $\lambda$ is detected regardless of the value of the temperature T. A multidimensional approximation may be used for this purpose to attain a higher accuracy.

Figures 16A, 16B:
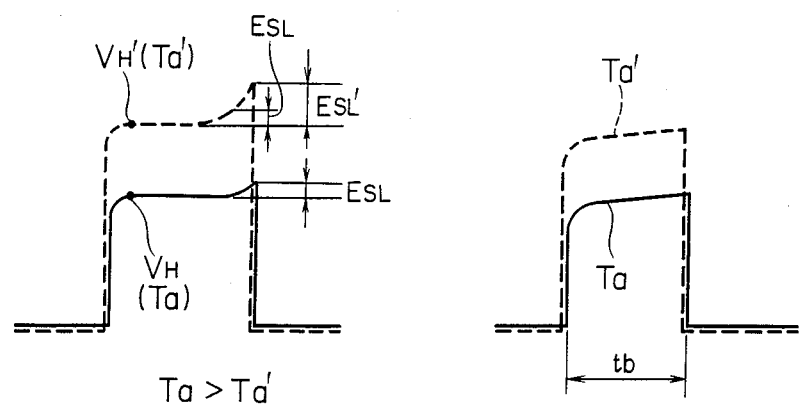
FIGS. 16A, 16B and 17 are diagrams showing an even still further embodiment.
Figure 17:
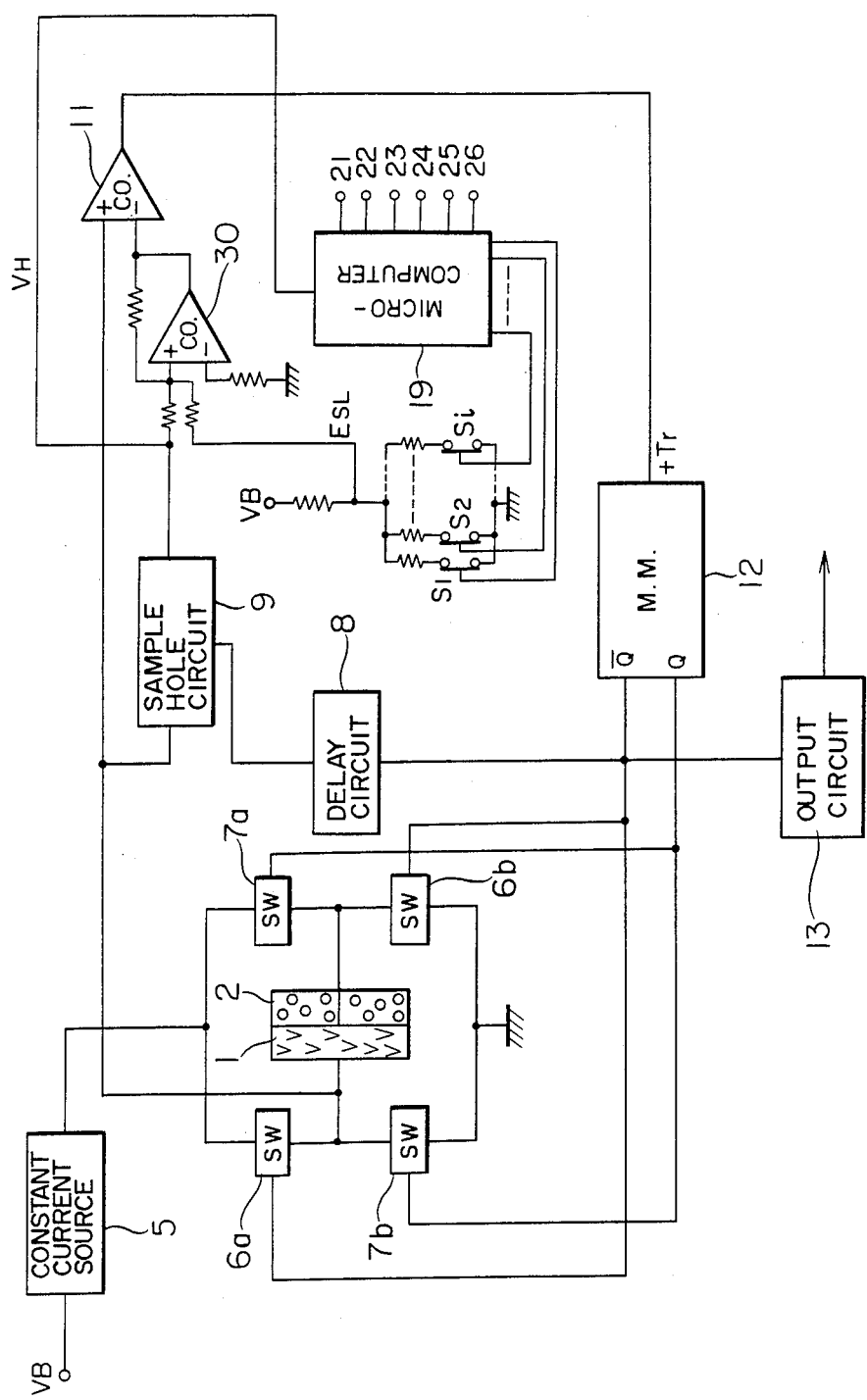

FIGS. 16A to 17 show another configuration of the temperature compensation circuit. In this embodiment, Ib, Is and $t_b$ are fixed, while $E_{SL}$ is changed for temperature compensation. Specifically, when the temperature is low, $E_{SL}$ is increased to $E_{SL}'$ to lengthen the sensing time, thus achieving the temperature compensation. FIG. 16A shows a waveform obtained during the sensing operation, and FIG. 16B a waveform for bias operation. As shown in FIG. 16A, if the ambient temperature is Ta', the sensing time is lengthened by increasing the value $E_{SL}$ to $E_{SL}'$ to make equal to that of Ta.

In FIG. 17, the value of $E_{SL}$ added to the voltage $V_H$ is changed by the operational amplifier 30 in accordance with the output of the microcomputer 19. The voltage $V_H$ held is introduced into the microcomputer 19. The value $E_{SL}$ determined by the voltage $V_H$ is taken out of the switches $S_1, S_2, \ldots S_i$ actuated in response to the output of the microcomputer 19. By changing the value $E_{SL}$ by the voltage $V_H$ in this manner, an output is produced without being affected by the temperature.

Figure 19:
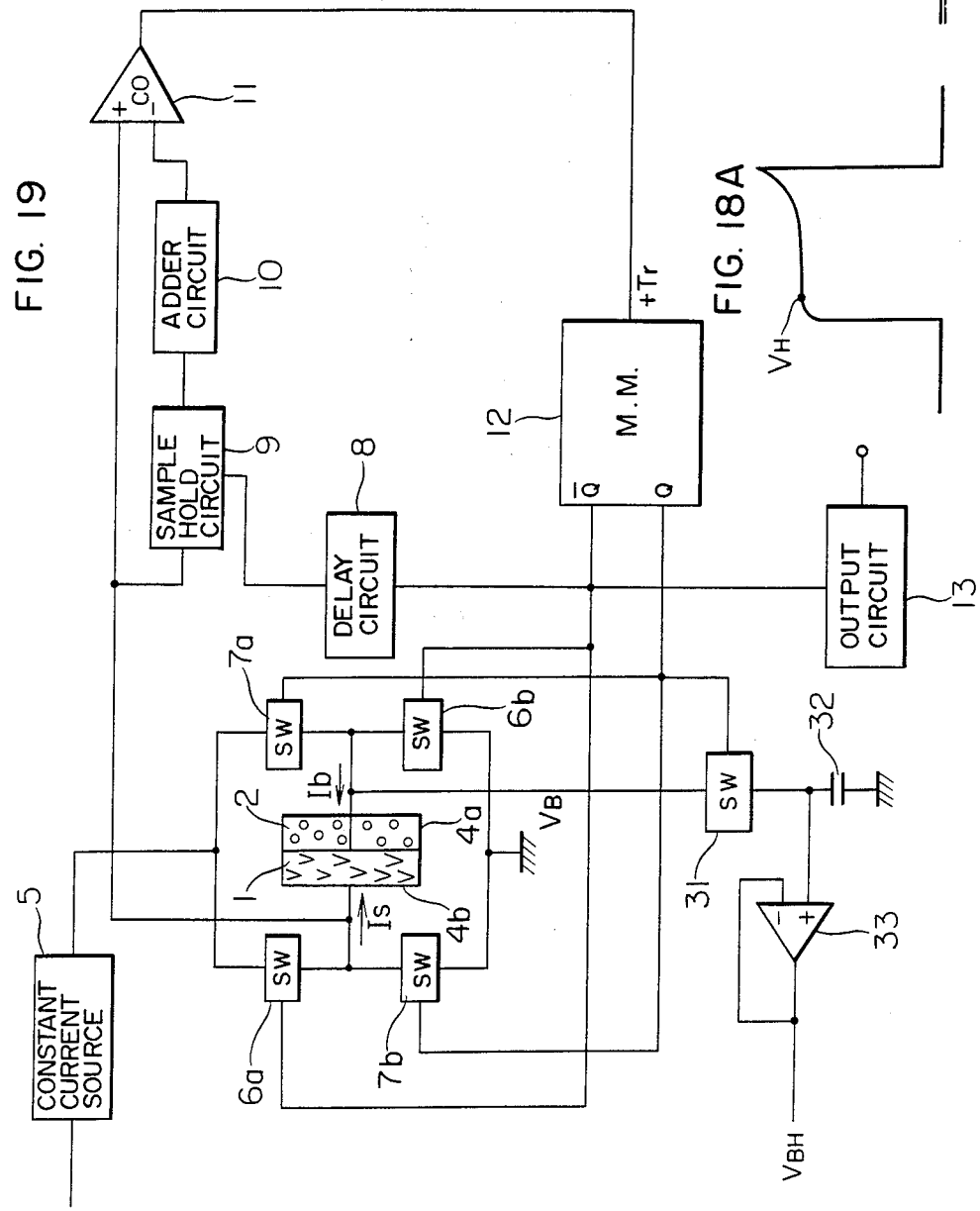
FIGS. 18A, 18B and 19 are diagrams showing a different embodiment.
Figure 18B:
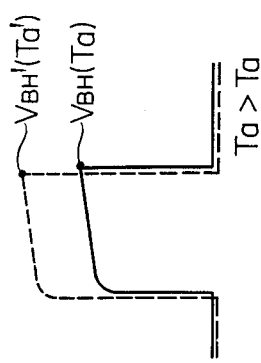
Figure 18A:
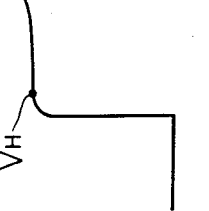

FIGS. 18A to 19 show another embodiment in which the terminal voltage $V_{BH}$ at the end of the bias operation (FIG. 18B) is used instead of the voltage $V_H$ for the sensing operation (FIG. 18A) as a temperature function signal. This voltage $V_{BH}$ is also substantially proportional to rI as seen from equation (1), because P(4a) is almost equal to P(4b).

FIG. 19 shows an embodiment of a circuit for holding the value $V_{BH}$. During the bias operation, the terminal Q of the multivibrator 12 is turned on. As a result, the switch 31 is also turned on, so that the capacitor 32 is kept charged with the terminal voltage $V_B$ for bias operation. At the end of the bias operation, the switch 31 is turned off, with the result that the final value of the terminal voltage is left charged in the capacitor 32. This value is produced as the voltage $V_{BH}$ through a buffer amplifier 33, which value $V_{BH}$ may be used as a temperature function signal for the above-mentioned temperature compensation circuit in the microcomputer 19.

Figure 20:
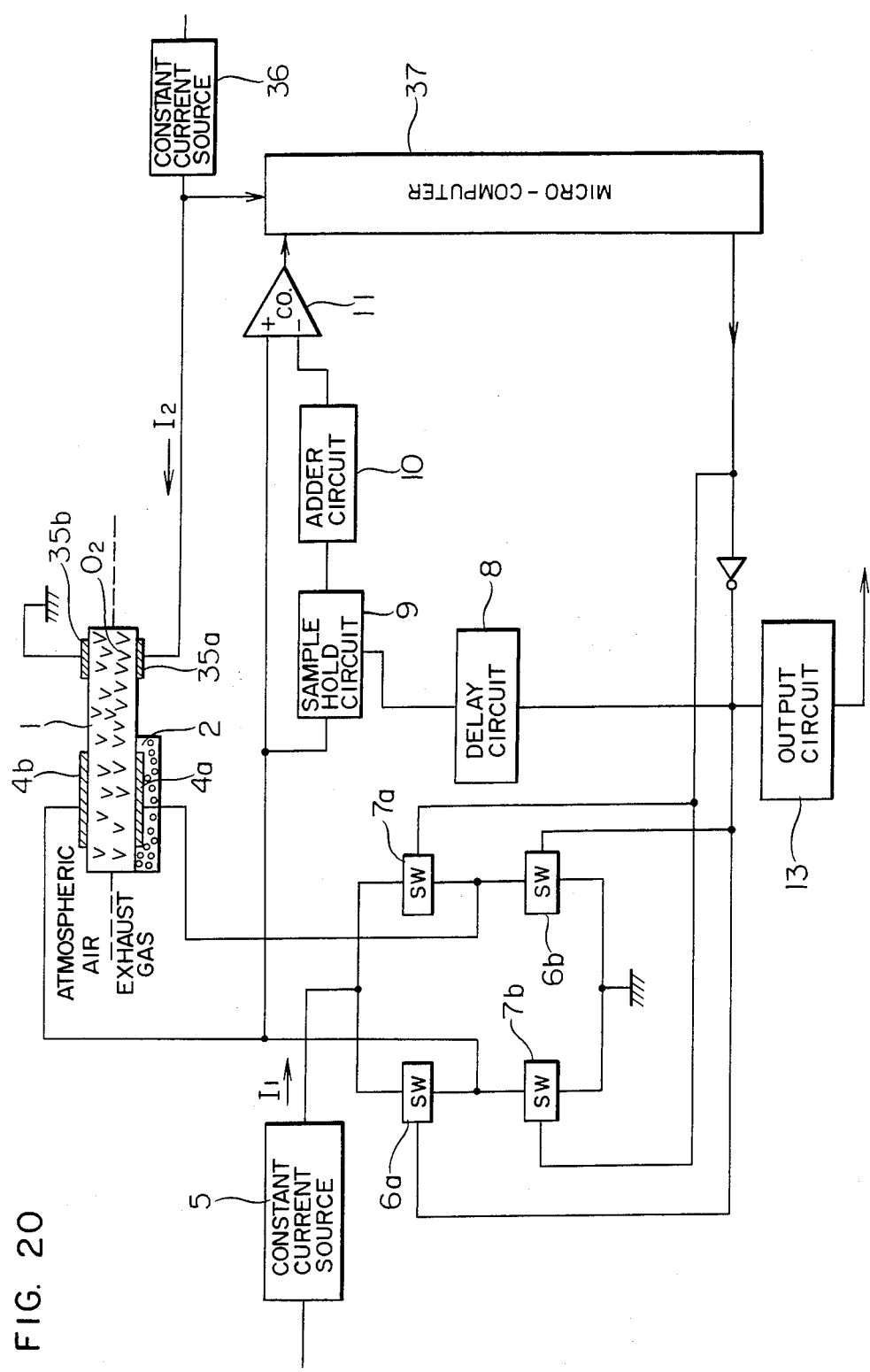
FIG. 20 is a diagram showing a still different embodiment.

FIG. 20 shows an embodiment of a configuration for producing the temperature function signal. In addition to the electrodes 4a and 4b for measuring the air-fuel ratio, electrodes 35a and 35b for measuring the internal resistance are disposed on the solid electrolyte 1. The current $I_2$ is supplied between the electrodes 35a and 35b by a constant current source 36. In this case, the electrode 35a is used as a positive electrode, and oxygen is applied from the atmospheric side to the exhaust side. From the constant current value $I_2$ and the voltage involved, the internal resistance of the solid electrolyte 1 is determined. In view of the fact that oxygen is supplied from the atmospheric side toward the exhaust side, it is possible to measure the internal resistance even when the oxygen concentration of the exhaust gas is small. Also, the value $I_2$ is required to be made smaller than the critical current value attributable to the diffusion resistance component of the atmosphere air path. This voltage value relating to the internal resistance is applied to the microcomputer 37 as a temperature function signal, thereby to perform the heater control as shown in FIG. 7 or the various corrections mentioned above. FIG. 20 shows an embodiment in which the bias time is corrected.

FIGS. 21A and 21B are diagrams showing an embodiment of another configuration for producing the temperature function signal. Specifically, the average value $V_{av}$ of the terminal voltage obtained during a measurement is used as a temperature function signal. The waveform of solid line shown in FIG. 21A represents the value of the terminal voltage, and the dotted line the average value $V_{av}$ used as a temperature function signal. This average value is obtained by digital time integration at the microcomputer 37. In another embodiment of a simpler configuration shown in FIG. 21B, only the terminal voltage for the sensing operation is applied to an integration circuit including a resistor 39 and a capacitor 40 through a switch 38 thereby to integrate the waveform thereof. After that, this value is held, and applied into the microcomputer 37 through a buffer amplifier 41. This input value is substantially the same as the voltage $V_{av}$ in FIG. 21A, and therefore the value $V_{av}$ may be used for various corrections including the heater control as mentioned above. In the embodiment shown in FIG. 21B, the bias time is changed.

Figures 22A, 22B:
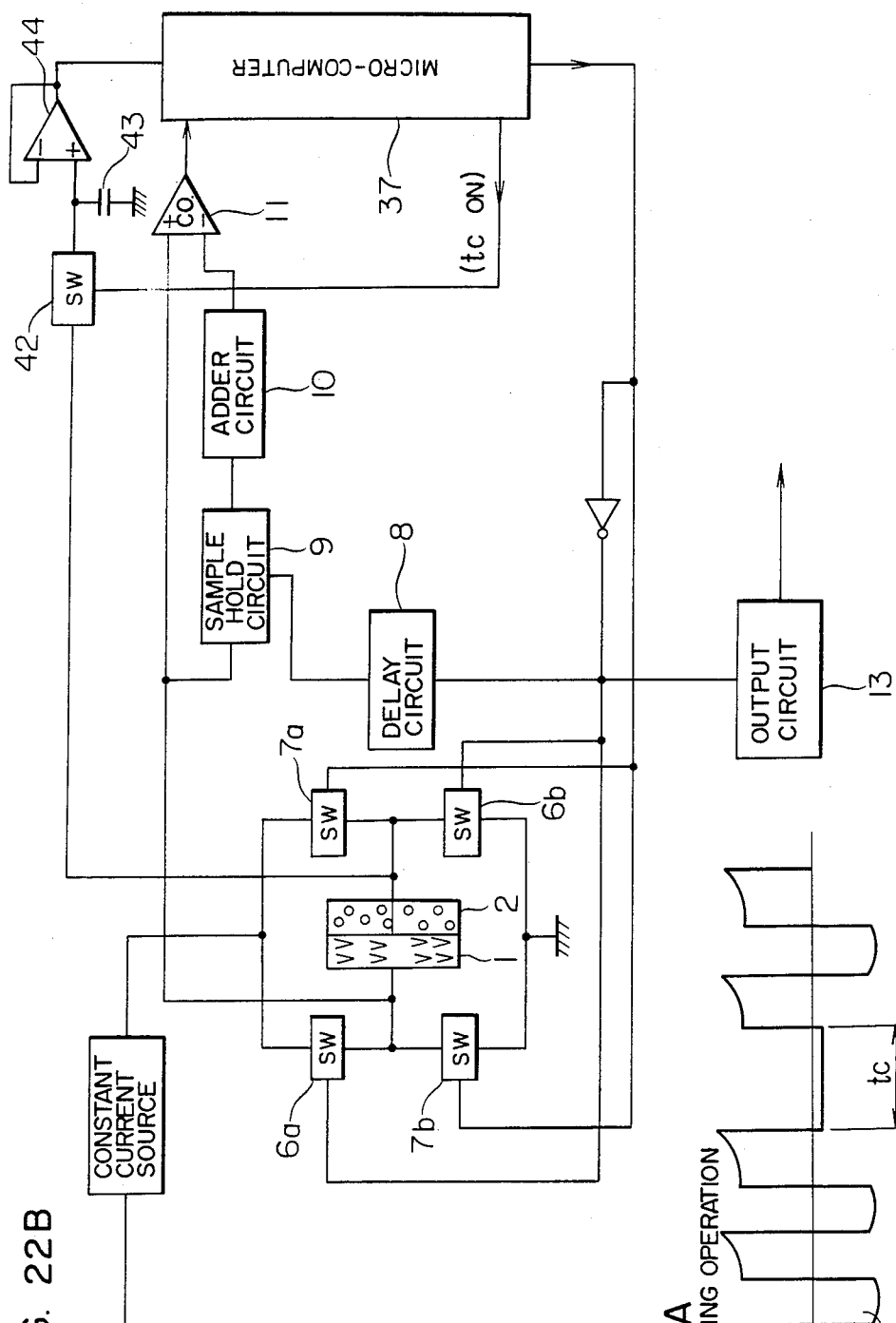
FIGS. 22A and 22B are diagrams showing an even still different embodiment.

As shown in FIG. 22A, a third period for the sole purpose of measuring the temperature is set, and by supplying a constant current to the solid electrolyte 1 during this period $t_c$, the internal resistance is measured. In FIG. 22B, during the period $t_c$, the switches 6a and 6b are turned off with the switches 7a and 7b off, thereby introducing oxygen into the exhaust gas from the atmosphere. Also, during this period $t_c$, the switch 42 is turned on, and the terminal voltage is held by the capacitor 43. This voltage is applied into the microcomputer 37 through the buffer amplifier 44. At the microcomputer 37, this signal is used for various correcting functions mentioned above including the heater control.

Figure 23:
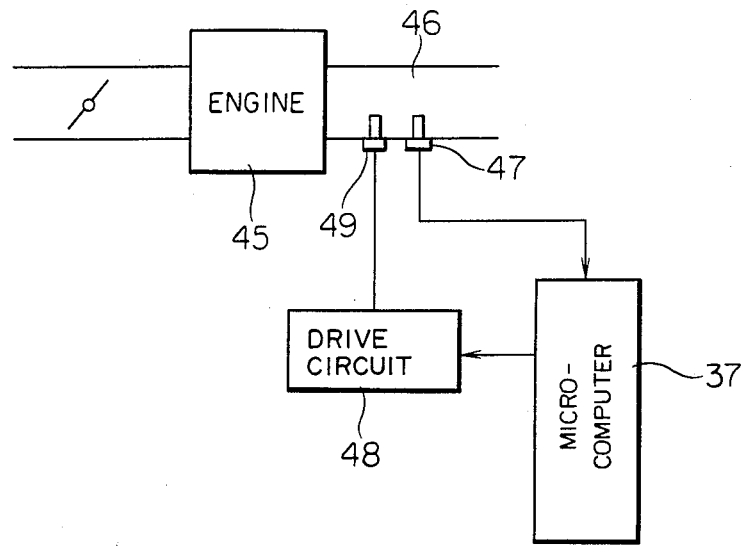
FIGS. 23 and 24. are diagrams showing other different embodiments.

FIG. 23 shows another configuration for producing a temperature function signal, in which an exhaust gas temperature sensor 47 is provided on an exhaust gas pipe 46 downstream of the engine 45, and the signal from this sensor 47 is used as a temperature function signal. This signal is applied to the microcomputer 37 thereby to apply various correction signals mentioned above to a drive circuit 48 of the air-fuel ratio sensor 49.

Figure 24:
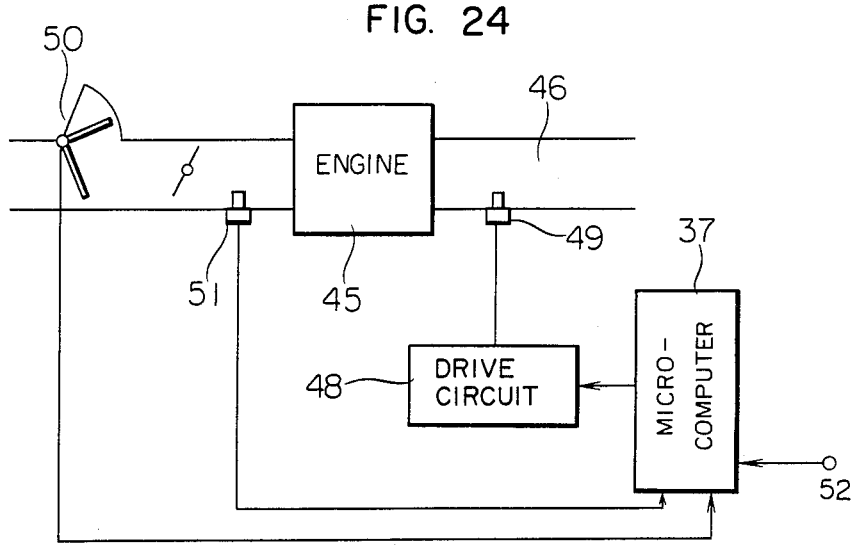

FIG. 24 shows another embodiment, in which the operating conditions of the engine 45 (engine speed and the load) are detected by means of an intake air amount sensor 50, an intake manifold negative pressure sensor 51 and an engine speed sensor 52. With these operating conditions as a temperature function signal, a correction signal is supplied to the drive circuit 48 of the air-fuel ratio sensor 49 for the purpose of temperature compensation.

Now, a method of determining the voltage increment $E_{SL}$ from the initial terminal voltage $V_H$ at the time of sensing operation will be disclosed.

Figure 25:
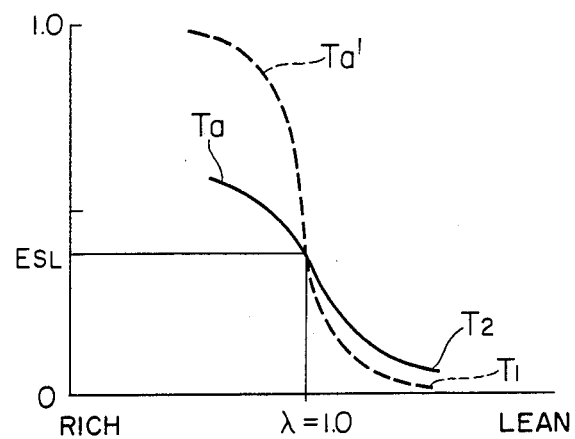
FIG. 25 is a diagram for explaining another principle of temperature compensation.

FIG. 25 is a diagram showing the relationship between the electromotive force between the sides of a solid electrolyte in contact with the atmosphere and the exhaust gas respectively and the air excess rate $\lambda$ of the exhaust gas. When the air excess rate of the exhaust gas is changed continuously, the electromotive force is changed stepwise at $\lambda=1.0$. FIG. 25 shows a voltage change in this process, where it changes stepwise between 0 and 1 V with $\lambda=1.0$ as a boundary. This change has a temperature characteristic, and the temperature Ta is higher than Ta'. Since the change rate of the electromotive force changes with temperature in this way, the sensor output is affected by the temperature if an improper value is set as $E_{SL}$. It is desirable to select the value $E_{SL}$ which is not affected by the temperature (Ta or Ta') (the point where both cross each other), that is, the value of $E_{SL}$ indicated in FIG. 4. This value normally exists between 0.2 V and 0.5 V. By selecting the value $E_{SL}$ thus free of temperature effect, an output value $t_s$ at which the influence of the temperature is reduced is obtained.

Figure 26:
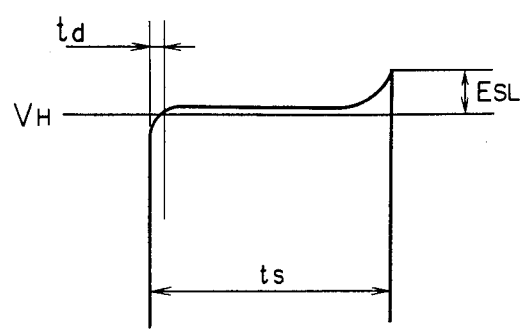
FIG. 26 is a diagram for explaining the setting of a hold voltage in the sensing period.

FIG. 26 shows another method of measuring the time $t_s$. For the purpose of circuit configuration, the point where the counting of the time $t_s$ is started is assumed to be located at the terminal voltage $V_H$ produced at a time point after the lapse of a very short time $t_d$ from the start of the sensing operation. That is to say, with the voltage $V_H$ held, the measurement may be stopped at a time point when the terminal voltage exceeds $V_H$ by the value equivalent to $E_{SL}$. The value $t_s$ under this condition is converted into an output value.

Figure 27:
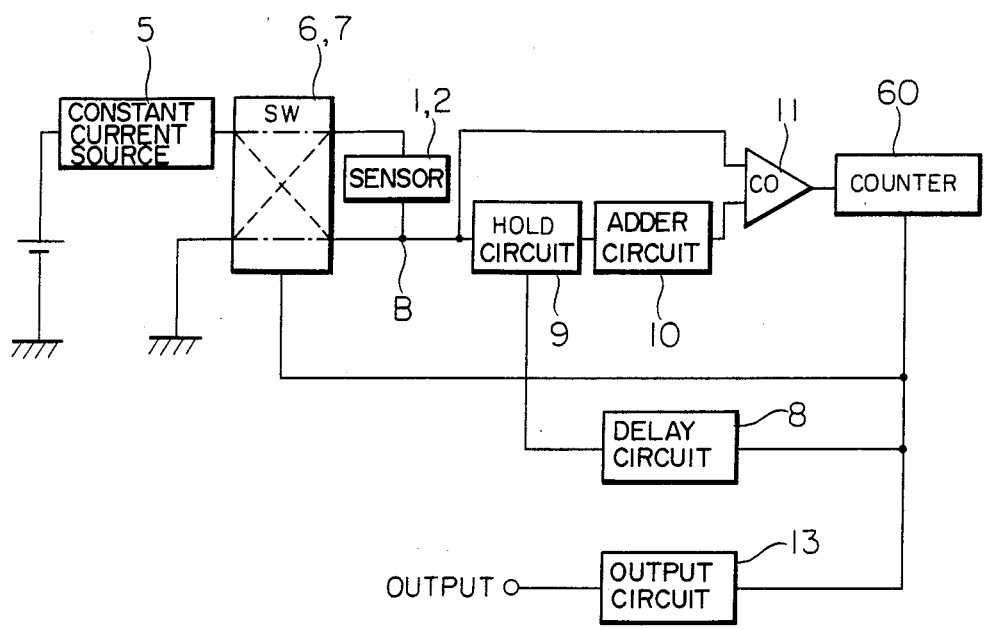
FIG. 27 is a diagram showing a general configuration of another embodiment of the present invention.
Figure 28:
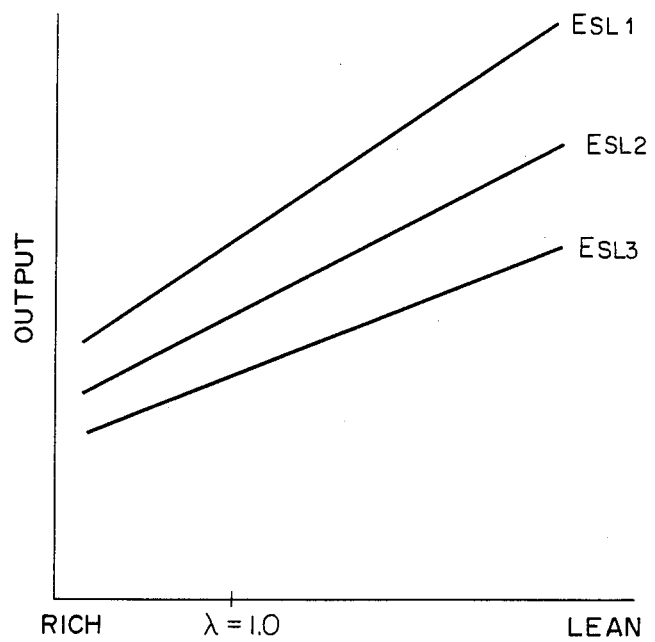
FIG. 28 is a diagram showing an actual example of characteristic variations with temperature.

FIG. 27 shows another embodiment of the sensor drive circuit. In FIG. 27, a constant current Is is supplied to the sensor 8 by means of a constant current source 6. Since Is is kept equal to Ib, one constant current source 6 is sufficient. The terminal from this constant current source and the grounding terminal are changed over by switches 6 and 7 to reverse the current flowing in the sensors 1 and 2. Assuming that the current Is is flowing at the time of sensing operation, the terminal voltage of the sensor 8 is supplied to the hold circuit 9 thereby to hold the voltage $V_H$. The time $t_d$ is counted by the delay line 13. The value $E_{SL}$ is added to the voltage $V_H$ by an adder circuit 10. When the terminal voltage V exceeds the level Vs+$E_{SL}$, a trigger signal is produced from the comparator 11. At the same time, an on signal is produced during the time $t_b$ from the counter 60, and the switches 6 and 7 are turned thereby to supply the current Ib in the direction opposite to the current Is in the sensor. After the lapse of time $t_b$, the action of the timer 60 turns off the on signal, and therefore the current Is begins to flow in the sensor again. The period of the on and off signals from the counter 60 is converted into a DC output by an output circuit 13. FIG. 28 shows the relationship between the value $\lambda$ and the output value, that is, the output characteristic with $E_{SL}$ changed to $E_{SL1}$, $E_{SL2}$, and $E_{SL3}$, in which $E_{SL1} > E_{SL2} > E_{SL3}$. Among these values of $E_{SL}$, a value is selected in FIG. 25 showing a characteristic free of the effect of temperature.

Figure 29A:
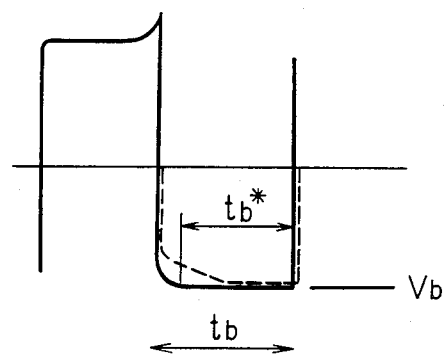
FIGS. 29A, 29B and 30 are diagrams showing still another embodiment of the present invention.
Figure 29B:
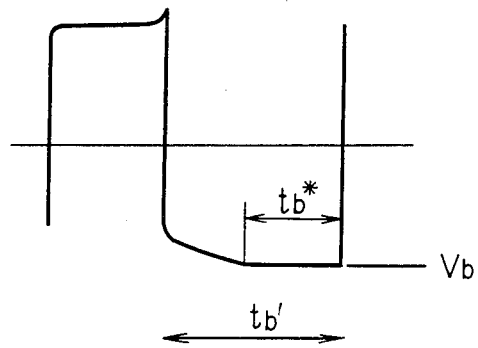
Figure 30:
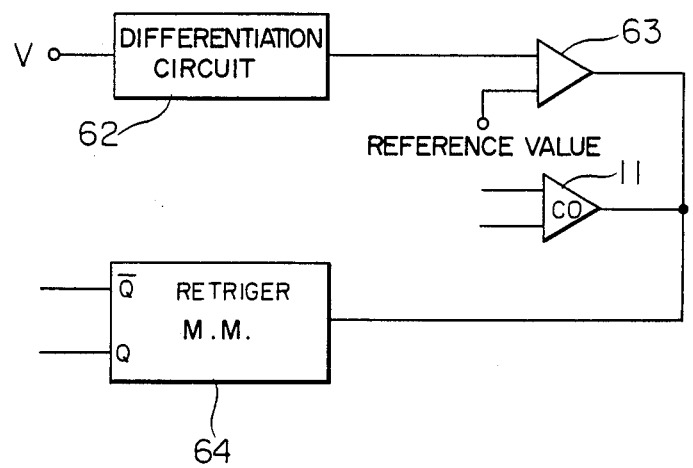

FIG. 29A shows an application where the oxygen bias is maintained always constant. If the time of the terminal voltage settling to a predetermined value Vb during the bias operation is delayed as shown by a dotted line in FIG. 29A, a lesser amount of oxygen is biased, affecting the output value. In order to avoid this inconvenience, the time $t_b^*$ after settlement to the predetermined value Vb is made the same by lengthening the bias time $t_b'$ as shown in FIG. 29B. In this way, the same amount of oxygen is biased all the time. The time $t_b^*$ begins to be counted from the time point where the change of the terminal voltage V with time dV/dt is reduced below a predetermined level. Specifically, as shown in FIG. 30, the voltage V is differentiated in a differentiation circuit 62, and after detection that it is reduced below a reference value at a comparator 63, a retrigger monotostable multivibrator 64 is actuated. The multivibrator 64 corresponds to the device 12 in FIG. 5, which is used for retrigger after the comparator 11.

According to the embodiment under consideration, therefore, it is possible to measure the air excess rate in all the regions from rich to lean state of the mixture gas without any temperature compensation.

It will thus be understood from the foregoing description that according to the present invention, a wide range of air excess rate is detected without being affected by temperature changes.

We claim:

1. In an air-fuel ratio detection system comprising a solid eletrolyte in contact with a diffusion resistor on one side and the atmosphere on the other side thereof, the oxygen concentration in said diffusion resistor being related to the oxygen concentration in the exhaust gas, the improvement comprising means for applying an electric current to said solid electrolyte to supply oxygen in the atmosphere into said diffusion resistor for at least a period of time until the amount of the oxygen introduced into said diffusion resistor through said solid electrolyte is balanced with the amount of the oxygen diffused into the exhaust gas through said diffusion resistor, means for subsequently applying a predetermined current of opposite polarity to said solid electrolyte thereby to draw oxygen out of said diffusion resistor, and means for detecting the air-fuel ratio on the basis of the time required for the voltage drop across the solid electrolyte to reach a predetermined value while drawing the oxygen out of the diffusion resistor.

2. A system according to claim 1, further comprising temperature compensation means for preventing the detected air-fuel ratio from being affected by the temperature.

3. A system according to claim 2, wherein said temperature compensation means includes means for detecting the operating conditions of the internal combustion engine, and means for correcting the air-fuel ratio in accordance with said operating conditions.

4. In an air-fuel ratio detection system comprising a solid electrolyte in contact with a diffusion resistor on one side and the atmosphere on the other side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, means for detecting the air-fuel ratio on the basis of the time required for the voltage drop across the solid electrolyte to reach a predetermined value while drawing the oxygen out of the diffusion resistor, and temperature compensation means for preventing the detected air-fuel ratio from being affected by the temperature, wherein said temperature compensation means includes means for detecting the voltage between the sides of the solid electrolyte in the initial stage of the drawing operation, and means for controlling the temperature of the solid electrolyte in such a manner as to maintain the detection voltage at a fixed value.

5. A system according to claim 4, wherein said temperature compensation means includes a comparator for comparing the detection voltage with a reference value and producing an output signal when the detection voltage is higher than the reference voltage, and heater means for heating the solid electrolyte upon application of the output signal thereto.

6. In an air-fuel ratio detection system comprising a solid electrolyte in contact with a diffusion resistor on one side and the atmosphere on the other side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, means for detecting the air-fuel ratio on the basis of the time required for the voltage drop across the solid electrolyte to reach a predetermined value while drawing the oxygen out of the diffusion resistor, and temperature compensation means for preventing the detected air-fuel ratio from being affected by the temperature, wherein said temperature compensation means includes means for detecting the voltage between the sides of the solid electrolyte in the initial stage of the oxygen drawing out operation, and means for controlling the oxygen supplying operation on the basis of the detection voltage.

7. A system according to claim 6, wherein said supplying operation control means includes means for detecting that the voltage between the sides of the solid electrolyte during the oxygen supplying operation coincides with the voltage in the initial stage of the oxygen drawing out operation, and means for terminating the oxygen supplying operation upon detection of the coincidence.

8. A system according to claim 6, wherein said supplying operation control means includes means for determining the time of the supplying operation in accordance with the oxygen voltage in the initial stage of the drawing out operation, and means for performing the oxygen supplying operation during a period of time determined by said determining means.

9. A system according to claim 6, wherein said oxygen supplying operation control means includes means for determining the magnitude of the current for performing the oxygen supplying operation in accordance with the voltage in the initial stage of the oxygen drawing out operation, and means for supplying said determined current to the solid electrolyte during the oxygen supplying operation.

10. A system according to claim 6, wherein said oxygen supplying operation control means includes means for selecting one of a plurality of predetermined characteristic curves in accordance with the voltage in the initial stage of the oxygen drawing out operation, and means for correcting a signal related to the oxygen drawing out time on the basis of the characteristic curve produced from said selection means.

11. In an air-fuel ratio detection system comprising a solid electrolyte in contact with a diffusion resistor on one side and the atmosphere on the other side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, and means for detecting the air-fuel ratio on the basis of the time required for the voltage drop across the solid electrolyte to reach a predetermined value while drawing the oxygen out of the diffusion resistor, further comprising means for setting said predetermined current.

12. A system according to claim 11, wherein said setting means includes means for detecting the voltage between the sides of said solid electrolyte in the initial stage of the oxygen drawing out operation, and means for adding a predetermined voltage to said detection voltage.

13. A system according to claim 12, wherein said predetermined voltage is set to a value which remains substantially unchanged with temperature when the air excess rate is 1.

14. A system according to claim 12, further comprising means for determining said predetermined voltage in accordance with the voltage in the initial stage of the oxygen drawing out operation.

15. In an air-fuel ratio detection system comprising a solid electrolyte in contact with a diffusion resistor on one side and the atmosphere on the other side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, means for detecting the air-fuel ratio on the basis of the time required for the voltage drop across the solid electrolyte to reach a predetermined value while drawing the oxygen out of the diffusion resistor, and temperature compensation means for preventing the detected air-fuel ratio from being affected by the temperature, wherein said temperature compensation means includes means for holding the voltage between the sides of the solid electrolyte at the end of said oxygen supplying operation, and means for correcting the detected air-fuel ratio on the basis of the holding voltage.

16. In an air-fuel ratio detection system comprising a solid electrolyte in contact with a diffusion resistor on one side and the atmosphere on the other side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, and means for detecting the air-fuel ratio on the basis of the time required of the voltage drop across the solid electrolyte to reach a predetermined value while drawing the oxygen out of the diffusion resistor, further comprising electrodes arranged on the atmosphere and exhaust sides of the solid electrolyte, means for supplying a predetermined value of current through said electrodes, means for generating a temperature compensation signal on the basis of the voltage produced between said electrodes, and means for correcting the detected air-fuel ratio on the basis of said temperature compensation signal.

17. In an air-fuel ratio detection system comprising a solid electrolyte in contact with a diffusion resistor on one side and the atmosphere on the other side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, means for detecting the air-fuel ratio on the basis of the time required for the voltage drop across the solid electrolyte to reach a predetermined value while drawing the oxygen out of the diffusion resistor, and temperature compensation means for preventing the detected air-fuel ratio from being affected by the temperatures, wherein said temperature compensation means includes means for determining an average value of the voltage between the sides of said solid electrolyte during the oxygen drawing out period, and means for correcting the detected air-fuel ratio on the basis of said average value.

18. In an air-fuel ratio detection system comprising a solid electrolyte in contact with a diffusion resistor on one side and the atmosphere on the other side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, means for detecting the air-fuel ratio on the basis of the time required for the voltage drop across the solid electrolyte to reach a predetermined value while drawing the oxygen out of the diffusion resistor, and temperature compensation means for preventing the detected air-fuel ratio from being affected by the temperature, wherein said temperature compensation means includes means for setting a temperature detection period in addition to the oxygen supplying time and the oxygen drawing out time, means for supplying a predetermined current in the direction of oxygen supply to the solid electrolyte during said temperature detection period, means for detecting the voltage between the sides of said solid electrolyte generated at the end of said temperature detection period, and means for correcting the detected air-fuel ratio on the basis of the detection voltage.

19. In an air-fuel ratio detection system comprising a solid electrolyte in contact with a diffusion resistor on one side and the atmosphere on the side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, means for detecting the air-fuel ratio on the basis of the time required for the voltage drop across the solid electrolyte to reach a predetermined value while drawing the oxygen out of the diffusion resistor, and temperature compensation means for preventing the detected air-fuel ratio from being affected by the temperature, wherein said temperature compensation means includes means for measuring the temperature of the exhaust pipe and means for correcting the detected air-fuel ratio on the basis of the temperature measurement.

20. In an air-fuel ratio detection system comprising a solid electrolyte in contact with a diffusion resistor on one side and the atmosphere on the other side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, and means for detecting the air-fuel ratio on the basis of the time required for the voltage drop across the solid electrolyte to reach a predetermined value while drawing the oxygen out of the diffusion resistor, wherein said supplying means includes means for detecting that the voltage between the sides of said solid electrolyte has increased to a predetermined value, and means for terminating the oxygen supplying operation with the lapse of a predetermined time following the time point of detection by said detection means.

21. An air-fuel ratio detection system comprising a solid electrolyte which permits conduction of oxygen ions therethrough, first and second electrodes arranged on the sides of said solid electrolyte, and a diffusion resistor arranged on said first electrode and exposed to a measurement gas, said system further comprising means for supplying oxygen to said first electrode through said solid electrolyte from said second electrode, means for drawing oxygen from the first electrode to said second electrode through said solid electrolyte, means for measuring the oxygen concentration in the measurement gas on the basis of an output signal indicating the movement of oxygen corresponding to the oxygen concentration of the measurement gas at the time of drawing the oxygen, means for producing a signal providing a temperature function of the solid electrolyte, and means for compensating for the effect of the ambient temperature on the solid electrolyte in response to the temperature function signal from said output means.

22. A system according to claim 21, wherein said temperature compensation signal is produced as an output signal at the time of drawing out the oxygen.

23. A system according to claim 21, further comprising a heater arranged on the second electrode side thereof, said compensation means controlling the current supplied to said heater.

24. A system according to claim 21, wherein said compensation means stops supplying the oxygen when the voltage with the oxygen supplied to the first electrode side has reached a voltage value obtained from said temperature function signal thereby to perform the temperature compensation.

25. A system according to claim 21, wherein said compensation means performs the temperature compensation by changing the time period during which oxygen is supplied to the first electrode side, by said temperature function signal.

26. A system according to claim 21, wherein said compensation means performs the temperature compensation by changing the current value applied to said solid electrolyte for supplying oxygen to the first electrolyte side, on the basis of the temperature function signal.

27. A system according to claim 21, wherein said compensation means stores the relationship between the air-fuel ratio and the output of the detector, and an air-fuel ratio is determined from the stored relationship on the basis of the temperature function signal, thereby to produce an output free of the effect of temperature.

28. A system according to claim 21, wherein said compensation means performs the temperature compensation by making variable the change of the terminal voltage for determining the time length of the oxygen drawing operation, on the basis of the temperature function signal.

29. A system according to claim 21, wherein said temperature function signal is obtained from the output signal of said solid electrolyte when oxygen is supplied to said first electrode.

30. A system according to claim 21, wherein said temperature function signal is obtained by measuring the internal resistance arranged on the solid electrolyte.

31. A system according to claim 21, wherein an average value of the terminal voltage over a given time period is used as the temperature function signal.

32. A system according to claim 21, wherein a third time period is provided for measuring the internal resistance of said solid electrolyte, and the internal resistance measured during said third time period is used as the temperature function signal.

33. A system according to claim 21, wherein the exhaust gas temperature of the engine is measured to obtain the temperature function signal.

34. A system according to claim 21, wherein the temperature function signal is obtained from the engine speed and load.

35. In an air-fuel ratio detection system comprising a solid electrolyte in contact with a diffusion resistor on one side and the atmosphere on the other side thereof, the oxygen concentration in said diffusion resistor being related to the oxygen concentration in the exhaust gas, the improvement comprising means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, and means for detecting the air-fuel ratio on the basis of the time required for the voltage drop across the solid electrolyte to reach a predetermined value while drawing the oxygen out of the diffusion resistor, wherein said diffusion resistor is a porous element.

36. An air-fuel ratio detection system comprising a single cell having a solid electrolyte in contact with a porous diffusion resistor on one side and the atmosphere on the other side thereof, the oxygen concentration in said diffusion resistor being related to the oxygen concentration in the exhaust gas, means for applying a predetermined current to said solid electrolyte for a predetermined period of time to supply oxygen in the atmosphere into said diffusion resistor, means for subsequently applying a predetermined current of opposite polarity to said solid electrolyte thereby to draw oxygen out of said diffusion resistor, and means for detecting the time required for the voltage drop across the solid electrolyte to reach a predetermined value while drawing the oxygen out of the diffusion resistor, said detected time being a measure of the air-fuel ratio.

* * * * *